US011717229B2

(12) United States Patent
Ojeda et al.

(10) Patent No.: US 11,717,229 B2
(45) Date of Patent: Aug. 8, 2023

(54) REAL-TIME PERIODIC ARTIFACT EXTRACTION FROM A PHYSIOLOGICAL SIGNAL

(71) Applicant: HI LLC, Los Angeles, CA (US)

(72) Inventors: Alejandro Ojeda, Culver City, CA (US); Husam Katnani, Braintree, MA (US)

(73) Assignee: HI LLC, Los Angeles, CA (US)

( * ) Notice: Subject to any disclaimer, the term of this patent is extended or adjusted under 35 U.S.C. 154(b) by 231 days.

(21) Appl. No.: 17/109,475

(22) Filed: Dec. 2, 2020

(65) Prior Publication Data

US 2021/0169424 A1 Jun. 10, 2021

Related U.S. Application Data

(60) Provisional application No. 62/967,120, filed on Jan. 29, 2020, provisional application No. 62/945,763, filed on Dec. 9, 2019.

(51) Int. Cl.
*A61B 5/00* (2006.01)
*A61B 5/024* (2006.01)

(52) U.S. Cl.
CPC .......... *A61B 5/7214* (2013.01); *A61B 5/0075* (2013.01); *A61B 5/0082* (2013.01); *A61B 5/024* (2013.01); *A61B 5/725* (2013.01)

(58) Field of Classification Search
CPC ... A61B 5/7214; A61B 5/0075; A61B 5/0082; A61B 5/024; A61B 5/725; A61B 5/14552; A61B 5/7203; A61B 5/7225; A61B 5/14553; A61B 5/0059; A61B 5/7207; G01N 21/359
See application file for complete search history.

(56) References Cited

U.S. PATENT DOCUMENTS

| 8,938,291 | B1 * | 1/2015 | Azarnasab | A61B 5/316 327/551 |
| 9,826,940 | B1 * | 11/2017 | Lengerich | A61B 5/721 |
| 2020/0205699 | A1 * | 7/2020 | McKay | A61B 5/6844 |

OTHER PUBLICATIONS

Li, H. and Zhao, H., "Instantaneous Heart Rate Detection using Smart Phones Built-in Camera", May 2016, Atlantis Press, Proceedings of the 2016 2nd Workshop on Advanced Research and Technology in Industry Applications, doi: 10.2991/wartia-16.2016.324 (Year: 2016).*

(Continued)

*Primary Examiner* — Colin T. Sakamoto
*Assistant Examiner* — Tommy T Ly
(74) *Attorney, Agent, or Firm* — Michael J. Bolan; Vista IP Law Group, LLP

(57) ABSTRACT

A physiological activity detection system comprises a signal acquisition module configured for non-invasively acquiring a signal from an anatomical structure of a user, the acquired signal having a physiological-encoded component and a periodic artifact component that dominates the physiological-encoded component. The physiological activity detection system further comprises a phase-locked loop (PLL) component configured for estimating a phase of the periodic artifact component of the acquired signal, and generating a periodic reference signal having a phase representative of the estimated phase of the periodic artifact component of the acquired signal.

40 Claims, 10 Drawing Sheets

(56) References Cited

OTHER PUBLICATIONS

Nguyen HD, Yoo SH, Bhutta MR, Hong KS. Adaptive filtering of physiological noises in fNIRS data. Biomed Eng Online. Dec. 4, 2018;17(1):180. doi: 10.1186/s12938-018-0613-2. PMID: 30514303; PMCID: PMC6278088. (Year: 2018).*

Trajkovic, I., Scholkmann, F., & Wolf, M., "Estimating and validating the interbeat intervals of the heart using near-infrared spectroscopy on the human forehead", Journal of Biomedical Optics, vol. 16(8)Aug. 2011; https://doi.org/10.1117/1.3606560; 10 pages.

Perdue, K. L,, Westerlund, A., McCormick, S. A., & Nelson, C. A., "Extraction of heart rate from functional near-infrared spectroscopy in infants", Journal of Biomedical Optics, vol. 19(6), Jun. 2014; https://doi.org/10.1117/1.jbo.19.6.067010; 9 pages.

Sun, J., Rao, L., & Gao, C., "Extracting heartrate from optical signal of functional near-infrared spectroscopy based on mathematical morphology", Journal of Innovative Optical Health Sciences, vol. 11. No. 3, Jan. 2, 2018; 1850010; https://doi.org/10.1142/S1793545818500104; 8 pages.

* cited by examiner

REAL-TIME PERIODIC ARTIFACT EXTRACTION FROM A PHYSIOLOGICAL SIGNAL

RELATED APPLICATION DATA

Pursuant to 35 U.S.C. § 119(e), this application claims the benefit of U.S. Provisional Application Ser. No. 62/945,763, filed Dec. 9, 2019, and U.S. Provisional Application Ser. No. 62/967,120, filed Jan. 29, 2020, which are expressly incorporated herein by reference.

FIELD OF THE INVENTION

The present inventions relate to methods and systems for non-invasive measurements in the human body, and in particular, methods and systems related to detecting physiological activity in the human body, animal body, and/or biological tissue.

BACKGROUND OF THE INVENTION

Measuring neural activity in the brain is useful for medical diagnostics, neuromodulation therapies, neuroengineering, or brain-computer interfacing. Conventional methods for measuring neural activity in the brain include diffusive optical measurement techniques, which employ moderate amounts of near-infrared or visible light radiation, thus being comparatively safe and gentle for a person in comparison to X-Ray Computed Tomography (CT) scans, positron emission tomography (PET), or other methods that use higher-energy and potentially harmful ionizing radiation. Moreover, in contrast to methods, such as functional magnetic resonance imaging (fMRI), these optically-based measurement methods do not require large magnets or magnetic shielding, and thus, can be scaled to wearable or portable form factors, which is especially important in brain-computer interface (BCI) applications that require subjects to interact freely within their environment.

Functional near-infrared spectroscopy (fNIRS) is an optically-based measurement technique that allows the indirect inference of cortical responses to stimuli. That is, the fNIRS technique measures the hemodynamic response (e.g., concentration changes in oxy-hemoglobin and deoxy-hemoglobin) of different cortical region in the brain, which can be used as a proxy for neural activity in the brain. In its most basic form, an fNIRS technique involves emitting light into the cortical region of the brain, which is neurologically encoded by hemodynamic responses in the brain and exits the brain as neurological-encoded signal light, and analyzing neurological-encoded signal light for the hemodynamic responses, and thus neural activity, in the cortical region of the brain.

fNIRS techniques have been used in cognitive neuroscience, disease, infant, and hyperscanning studies (see L. Zhang, J. Sun, B. Sun, C. Gao, H. Gong, "Detecting Bilateral Functional Connectivity in the Prefrontal Cortex During a Stroop Task by Near-Infrared Spectroscopy," *J. Innov. Opt. Health Sci.* 6, 1350031 (2013); J. Sun, B. Sun, L. Zhang, Q. Luo, H. Gong, "Correlation Between Hemodynamic and Electrophysiological Signals Dissociates Neural Correlates of Conflict Detection and Resolution in a Stroop Task: A Simultaneous Near-Infrared Spectroscopy and Event related Potential Study," *J. Biomed. Opt.* 18, 096014-096014 (2013); C. Gao, J. Sun, X. Yang, H. Gong, "Gender Differences in Brain Networks During Verbal Sternberg Tasks: A Simultaneous Near-Infrared Spectroscopy and Electro-Encephalography Study," *J. Biophoton* (2017); Z. Zhang, M. Schneider, U. Fritschi, I. Lehner, R. Khatami, "Near-Infrared Spectroscopy (NIRS) as a Useful Tool to Evaluate the Treatment Efficacy of Positive Airways Pressure Therapy in Patients with Obstructive Sleep Apnea Syndrome (OSAS): A Pilot Study," *J. Innov. Opt. Health Sci.* 7, 342-345 (2014); M. Ferrari, V. Quaresima, "A Brief Review on the History of Human Functional Near-Infrared Spectroscopy (fNIRS) Development and Fields of Application," *Neuroimage* 63, 921-935 (2012); X. Cui, D. M. Bryant, A. L. Reiss, "NIRS-Based Hyperscanning Reveals Increased Interpersonal Coherence in Superior Frontal Cortex During Cooperation," *Neuroimage* 59, 2430-2437 (2012)).

The fNIRS signal acquired from a brain is highly sensitive to physiological signals originating from outside the brain. In studies that focus on hemodynamics as a proxy for neural activity, heartbeat has been shown to dominate and mask the neurological-encoded component of the fNIRS signal, and manifests itself as a cardiac artifact in the fNIRS signal (see Sun, B. Sun, L. Zhang, Q. Luo, H. Gong, "Correlation Between Hemodynamic and Electrophysiological Signals Dissociates Neural Correlates of Conflict Detection and Resolution in a Stroop Task: A Simultaneous Near-Infrared Spectroscopy and Event related Potential Study," *J. Biomed. Opt.* 18, 096014-096014 (2013); and T. J. Huppert, S. G. Diamond, M. A. Franceschini, D. A. Boas, "HomER: A Review of Time-Series Analysis Methods for Near-Infrared Spectroscopy of the Brain," *Appl. Opt.* 48, D280-D298 (2009)).

Some neural applications consider heartbeat to be a source of noise, in which case, it is desirable to identify and remove cardiac artifacts from the fNIRS signal. Other neural applications treat heart rate (HR) as useful information. For example, in response to various task conditions provided to a subject (e.g., an infant), the HR can provide information on the state of a subject, e.g., to provide a view of the autonomic system of the subject that complements the view of the central nervous system of the subject provided by the neurological-encoded component in the fNIRS signal. Furthermore, the HR may provide a measure of heart rate variability (HRV), which can be indicative of the attention and orienting of the subject, and thus, how the subject perceives the task. As another example, HR is believed to be modulated by subcortical structures that are not accessible with an fNIRS technique, and therefore, the HR can provide complementary information to the neurological-encoded signal acquired in the fNIRS technique (see Perdue, K. L., Westerlund, A., McCormick, S. A., & Nelson, C. A. (2014). "Extraction of Heart Rate from Functional Near-Infrared Spectroscopy in Infants." *Journal of Biomedical Optics,* 19(6), 067010 (June 2014)). As still another example, the HR and neurological-encoded signal can be used to verify the elicitation of stress in a subject (see M. Tanida, M. Katsuyama, "Relation Between Mental Stress-Induced Prefrontal Cortex Activity and Skin Conditions: A Near-Infrared Spectroscopy Study," *Brain Res.* 1184, 210-216 (2008)).

Typically, HR is measured with electrocardiography (ECG), and is calculated by finding the time difference between subsequent R waves (R-R intervals) in the QRS complex. While there is no technical reason why simultaneous ECG and fNIRS measurements cannot be separately performed, in practice this involves detailed and more costly setup procedures, including optodes placed on the head and electrodes placed on the chest, which may increase discomfort for the subjects. Furthermore, this setup is far from ideal when studying infants or young children, who have very limited attention spans and ability to regulate their emotions.

Thus, in the case where HR is treated as useful information, extracting an HR component from an fNIRS signal would be preferable to separately acquiring an ECG and an fNIRS signal from a subject (see Perdue, K. L., Westerlund, A., McCormick, S. A., & Nelson, C. A. (2014). "Extraction of Heart Rate from Functional Near-Infrared Spectroscopy in Infants." *Journal of Biomedical Optics*, 19(6), 067010 (June 2014).

Although several techniques have been proposed for removing cardiac artifacts (either as noise or as a useful HR component) from an fNIRS signal, the translation of these techniques to real-time applications, such as BCI applications, is challenging.

One technique for extracting cardiac artifacts from an fNIRS signal employs an empirical mode decomposition (EMD) of fNIRS data, which can be visually inspected to extract the cardiac artifacts from the fNIRS data (see Trajkovic, I., Scholkmann, F., & Wolf, M. "Estimating and Validating the Interbeat Intervals of the Heart Using Near-Infrared Spectroscopy on the Human Forehead. *Journal of Biomedical Optics*, 16(8), 087002 (August 2011)). Another technique estimates the HR from fNIRS data by identifying the channels (i.e., frequencies) affected by the cardiac artifacts as those having peaks in the power spectral density between 1.5 Hz and 3.5 Hz, applies a band-pass filter to the affected channels between 1.5 Hz and 4.0 Hz, applying a peak finding algorithm to the output of the band-pass filter, and then computing the inverse of the temporal distance between the consecutive peaks as the HR (see Perdue, K. L., Westerlund, A., McCormick, S. A., & Nelson, C. A. (2014). "Extraction of Heart Rate from Functional Near-Infrared Spectroscopy in Infants." *Journal of Biomedical Optics*, 19(6), 067010 (June 2014)). Still another technique uses morphological operators to extract cardiac artifacts from fNIRS data, and estimating the HR using a peak finding algorithm similar to Perdue (see Sun, J., Rao, L., & Gao, C. (2018). "Extracting Heartrate From Optical Signal of Functional Near-Infrared Spectroscopy Based on Mathematical Morphology." *Journal of Innovative Optical Health Sciences*, 11(03), 1850010).

The techniques proposed by Traikovic and Sun require user intervention or operate in batch mode on relatively long segments of data, and thus, can only be effectively used in off-line neural applications. Although the technique proposed by Perdue can be used in an on-line neural application, Perdue uses a conventional signal processing approach to extract narrow-band oscillations (in this case, the cardiac artifacts) in the form of a band-pass filter, which has the drawback of distorting the neurological-encoded component in the fNIRS signal and introducing time delays in the processing pipeline, and thus, would not be very effective in real-time applications, such as a BCI application.

Another technique utilizes an adaptive filter to reject alternating current (AC) supply noise from a recording of a heart beat (i.e., an ECG). Instead of using a notch filter that may excessively degrade the quality of the ECG due to the heartbeat having frequency components that likely fall within the rejected range, this technique proposes the use of an adaptive filter that tracks the frequency of the noise from the AC supply as it fluctuates, subtracts the noise from the ECG recording, and outputs a relatively noise-free ECG signal. In this manner, this adaptive technique allows the filter to have a smaller rejection range, thereby improving the quality of the ECG signal output by the filter. While this technique may be effective for removing AC supply noise from an ECG signal in real-time, it requires separate inputs from the source of noise (in this case, the AC supply noise) and the biological signal of interest (in this case, the ECG). Thus, this technique is not effective in cases where it is desirable to extract a periodic artifact from a detected physiological signal, e.g., a cardiac artifact from an fNIRS signal, which as discussed above with respect to the previous techniques proposed by Trakovic, Perdue, and Sun, would otherwise minimize setup cost and effort, as well as discomfort to the person.

There, thus, remains a need to provide a means for effectively extracting a periodic artifact (e.g., a cardiac artifact) from a physiological signal (e.g., an optical signal having a neurological-encoded component) in real-time without independently acquiring the physiological signal and the periodic artifact from a person.

SUMMARY OF THE INVENTION

In accordance with one aspect of the present inventions, a physiological activity detection system comprises a signal acquisition module configured for non-invasively acquiring a signal from an anatomical structure of a user. The acquired signal may comprise, e.g., signal light. In this case, the signal acquisition module may be configured for non-invasively acquiring the signal light from the user via functional near-infrared spectroscopy (fNIRS). The acquired signal has a physiological-encoded component and a periodic artifact component that dominates the physiological-encoded component. In one embodiment, the anatomical structure of the user is a brain, in which case, the physiological-encoded component may be neurological-encoded component, and the periodic artifact component may be a cardiac artifact component.

The physiological activity detection system further comprises a phase-locked loop (PLL) component configured for estimating a phase of the periodic artifact component of the acquired signal, and generating a periodic reference signal (e.g., one that varies in accordance with a sine wave) having a phase representative of the estimated phase of the periodic artifact component of the acquired signal.

In one embodiment, the signal acquisition module is configured for digitizing the acquired signal into acquired data, and the PLL component is configured for estimating the phase of the periodic artifact component in the acquired data, and generating periodic reference data having a phase representative of the estimated phase of the periodic artifact component in the acquired data. For example, the acquired data may comprise a time-series of data samples, in which case, the PLL component may configured for respectively estimating phases of the periodic artifact component in the acquired data samples, and generating periodic reference data samples respectively having phases representative of the estimated phases of the periodic artifact component in the acquired data samples.

In one embodiment, the PLL component comprises a phase comparator and a voltage-controlled oscillator (VCO) arranged in a closed feedback loop with the phase comparator. The phase comparator is configured for computing a difference between the phase of the periodic artifact component of the acquired signal and the phase of the periodic reference signal, thereby respectively generating a phase error signal. The VCO is configured for generating the periodic reference signal, and varying the frequency of the periodic reference signal in accordance with the phase error signal, thereby varying the phase of the periodic reference signal.

In an optional embodiment, the physiological activity detection system further comprises a frequency computation component configured for computing a frequency of the periodic artifact component. For example, the periodic artifact component may be cardiac artifact component, in which case, the frequency computation component is a heart rate (HR) computation component, and the computed frequency of the cardiac artifact component is a heart rate (HR) of the user.

In another optional embodiment, the physiological activity detection system further comprises an artifact cancellation component configured for filtering the periodic artifact component from the acquired signal in accordance with a variable transfer function based on the periodic reference signal, thereby yielding a reduced-artifact signal. In this case, the physiological-encoded component may dominate the periodic artifact component in the reduced-artifact signal, and fact, be substantially eliminated from the reduced-artifact signal. The artifact cancellation component may optionally be configured for utilizing a recursive least squares (RLS) algorithm to vary the transfer function.

The physiological activity detection system may further comprise a signal processor configured for determining an existence of physiological activity in the user based on the reduced-artifact signal. If the anatomical structure of the user is a brain, the physiological-encoded component may be a neurological-encoded component, in which case, the physiological activity may be neural activity. The neural activity may be within cortical region of the brain of the user, in which case, the periodic artifact component may be cardiac artifact component, and the physiological activity detection system may further comprise a heart rate (HR) computation component configured for computing a heart rate (HR) of the user based on the phase of the periodic reference signal. The signal processor may be configured for determining an existence of neural activity in subcortical region of the brain of the user based on the computed HR of the user.

In one embodiment, the artifact cancellation component comprises a first signal comparator, an adaptive filter arranged in a feedback loop with the first signal comparator, and a second signal comparator. The first signal comparator is configured for computing a difference between a magnitude of an estimated periodic artifact component and a magnitude of the periodic reference signal, thereby generating a magnitude error signal. The adaptive filter is configured for varying the transfer function in response to the magnitude error signal, and filtering the acquired signal in accordance with the varied transfer function, thereby generating the estimated periodic artifact component. The second signal comparator is configured for computing the difference between a magnitude of the acquired signal and a magnitude of the estimated periodic artifact component to yield the reduced-artifact signal.

In another embodiment, the artifact cancellation component comprises a signal comparator and an adaptive filter arranged in a feedback loop with the first signal comparator. In this case, the signal comparator is configured for computing a difference between a magnitude of the acquired signal and a magnitude of an estimated periodic artifact component, thereby generating a magnitude error signal representative of the reduced-artifact signal, and the adaptive filter is configured for varying the transfer function in response to the magnitude error signal, and filtering the periodic reference signal in accordance with the varied transfer function, thereby generating the estimated periodic artifact component.

In accordance another aspect of the present inventions, a method of detecting physiological activity in an anatomical structure of a person comprises non-invasively acquiring a signal from the anatomical structure of the person. The acquired signal may comprise, e.g., signal light. In this case, the signal light may be non-invasively acquired from the user via functional near-infrared spectroscopy (fNIRS). The acquired signal has a physiological-encoded component and a periodic artifact component that dominates the physiological-encoded component. In one method, the anatomical structure of the user is a brain, in which case, the physiological-encoded component may be neurological-encoded component, and the periodic artifact component may be a cardiac artifact component.

The method further comprises computing a difference between an actual phase of the periodic artifact component of the acquired signal and an estimated phase of the periodic artifact component of the acquired signal, thereby generating a phase error signal, updating the estimated phase of the periodic artifact component of the acquired signal based on the phase error signal, repeating the phase different computation and estimated phase updating steps, and generating a periodic reference signal (e.g., one that varies in accordance with a sine wave) having a phase equal to the estimated phase of the periodic artifact component of the acquired signal.

One method further comprises digitizing the acquired signal into acquired data, in which case, the periodic reference signal may comprise periodic reference data. The acquired data may comprise a time-series of acquired data samples, in which case, the periodic reference data may comprise a time-series of periodic reference data samples.

In another method, the phase error generation step and estimated phase updating step comprises computing a difference between the phase of the periodic artifact component of the acquired signal and the phase of the periodic reference signal, thereby respectively generating the phase error signal, and varying the frequency of the periodic reference signal in accordance with the phase error signal, thereby varying the phase of the periodic reference signal.

An optional method further comprises deriving a frequency of the periodic artifact component from the phase of the periodic reference signal. For example, the periodic artifact component may be cardiac artifact component, in which case, the frequency computation component is a heart rate (HR) computation component, and the computed frequency of the cardiac artifact component is a heart rate (HR) of the user.

Another optional embodiment further comprises removing at least a portion of the periodic artifact component from the acquired signal, thereby yielding a reduced-artifact signal. In this case, the physiological-encoded component may dominate the periodic artifact component in the reduced-artifact signal, and fact, be substantially eliminated from the reduced-artifact signal. This optional method may utilize a recursive least squares (RLS) algorithm to vary the transfer function. This optional method may further comprise determining an existence of physiological activity in the user based on the reduced-artifact signal.

If the anatomical structure of the user is a brain, the physiological-encoded component may be a neurological-encoded component, in which case, the physiological activity may be neural activity. The neural activity may be within cortical region of the brain of the user, in which case, the periodic artifact component may be cardiac artifact component, and the method may further computing a heart rate (HR) of the user based on the phase of the periodic reference signal, and determining an existence of neural activity in subcortical region of the brain of the user based on the computed HR of the user.

In one method, removing at least a portion of the periodic artifact component from the acquired signal comprises computing a difference between a magnitude of an estimated periodic artifact component and a magnitude of the periodic reference signal, thereby generating a magnitude error signal, varying the transfer function in response to the magnitude error signal, filtering the acquired signal in accordance with the varied transfer function, thereby generating the estimated periodic artifact component, and computing the difference between a magnitude of the acquired signal and a magnitude of the estimated periodic artifact component to yield the reduced-artifact signal.

In another method, removing at least a portion of the periodic artifact component from the acquired signal comprises computing a difference between a magnitude of the acquired signal and a magnitude of an estimated periodic artifact component, thereby generating a magnitude error signal representative of the reduced-artifact signal, varying a transfer function in response to the magnitude error signal, and filtering the periodic reference signal in accordance with the varied transfer function, thereby generating the estimated periodic artifact component.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings.

Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
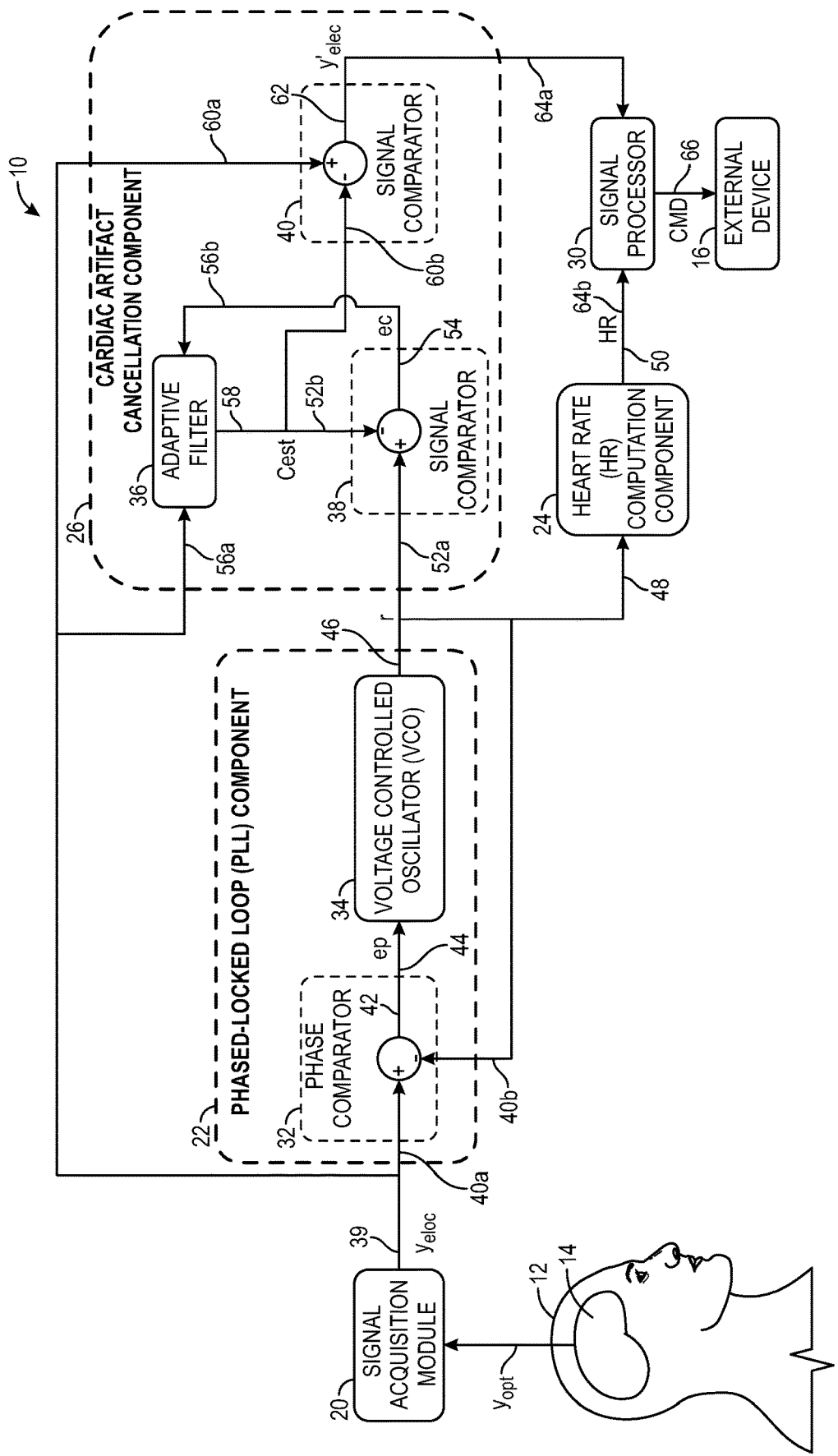
FIG. 1 is a block diagram of a neural activity detection system constructed in accordance with one embodiment of the present inventions.

A neural activity detection system (and variations thereof) described herein may form a portion of a brain computer interface (BCI) (also known as a neural-controlled interface (NCI), mind-machine interface (MMI), direct neural interface (DNI), or brain-machine interface (BMI)), which converts the neural activity information into commands that are output to an external device or devices for carrying out desired actions that replace, restore, enhance, supplement, or improve natural central nervous system (CNS) output, and thereby changes the ongoing interactions between the CNS of a user and an external or internal environment.

The neural activity detection system described herein is configured for, in real-time with little or no delay, non-invasively acquiring a signal containing a neurological-encoded component and a cardiac artifact component from a brain of the user, and reconstructing the neurological-encoded component and the cardiac artifact component from the acquired signal. The neural activity detection system is further configured for identifying the occurrence, extent of, and location of neural activity within the cortical structures of the brain of the user based on the neurological-encoded component, and deriving heart rate (HR) information from the cardiac artifact component, thereby obviating the need to independently acquire a neurological-encoded signal and a cardiac signal separately from the user using additional sensors and associated wires, i.e., a neurological-encoded signal and a cardiac signal can be acquired from one measurement using the neural activity detection systems described herein.

The neural activity detection systems described herein may be further configured for using the derived HR information to reconstruct the cardiac artifact component from the acquired signal, thereby producing a clean, and substantially undistorted, neurological-encoded signal from which the occurrence, extent of, and location of the neural activity within the cortical structures of the brain of the user can be derived. The neural activity detection systems may alternatively or optionally be further configured for using the derived HR information for other purposes, including, but not limited to, providing information (e.g., the existence of neural activity in the sub-cortical structures of the brain of the user) that is complementary to the neural activity information associated with the cortical structures of the brain of the user derived from the clean and undistorted neurological-encoded signal.

It should be appreciated that, although a neural activity detection system is described herein for use in a BCI, the present inventions should not be limited to neural activity measurements and BCIs, and may be applied to any system used for any application (including, but not limited to, medical, entertainment, neuromodulation stimulation, lie detection devices, alarm, educational, etc.), where it is desirable to process a signal acquired from any anatomical structure of a user, and which contains any periodic artifact component (whether from a biological source or an artificial source) that dominates a physiological-encoded component of interest of the acquired signal. For example, instead of deriving HR information from a neurological-encoded signal acquiring from a brain of the user, a periodic artifact component in the form of alternating current (AC) line noise from a power supply can be derived from an acquired signal containing a physiologically-encoded signal in the form of an electrocardiogram (ECG).

To minimize the size, weight, and cost of the headset (described in further detail below) used to acquire the signal from the brain of the user, the neural activity detection system described herein transforms the acquired signal, and thus the neurological-encoded component and cardiac artifact component, into data by digitally sampling the acquired signal, which data samples are then processed digitally in real-time (i.e., on a sample-by-sample basis) to reconstruct the neurological-encoded component and the cardiac artifact component from the transformed data. However, it should be appreciated that the signal acquired from the brain of the user may alternatively be at least partially processed in an analog fashion to ultimately reconstruct the neurological-encoded component and cardiac artifact component from the acquired signal.

The neural activity detection system described herein uses the signal acquired from the brain of the user to detect hemodynamic changes (and in this case, concentration changes in oxy-hemoglobin and deoxy-hemoglobin) in the cortical region of the brain of the user as a proxy for neural activity. However, alternative embodiments of the neural activity detection systems may acquire other types of signals as a proxy for neural activity, including, but not limited to, fast-optical signals (i.e., perturbations due to changes in the optical properties of neural tissue caused by mechanisms related to the depolarization of neural tissue, including, but not limited to, cell swelling, cell volume change, changes in membrane potential, changes in membrane geometry, ion redistribution, birefringence changes, macroscopic motion, change in mechanical stiffness of tissue, etc.), and other types of hemodynamic changes, e.g., Doppler shift due to moving blood flow, changes in blood volume, metabolism variations such a blood oxygen changes, etc.

The neural activity detection system described herein uses an fNIRS technique to obtain neural activity information from the signal acquired from the brain. However, it should be appreciated that alternative embodiments of the neural activity detection system may use any optically-based modality to obtain neural activity information, e.g., such as those described in U.S. patent application Ser. No. 15/844,370, entitled "Pulsed Ultrasound Modulated Optical Tomography Using Lock-In Camera" (now U.S. Pat. No. 10,335,036), U.S. patent application Ser. No. 15/844,398, entitled "Pulsed Ultrasound Modulated Optical Tomography With Increased Optical/Ultrasound Pulse Ratio" (now U.S. Pat. No. 10,299,682), U.S. patent application Ser. No. 15/844,411, entitled "Optical Detection System For Determining Neural Activity in Brain Based on Water Concentration" (now U.S. Pat. No. 10,420,469), U.S. patent application Ser. No. 15/853,209, entitled "System and Method For Simultaneously Detecting Phase Modulated Optical Signals" (now U.S. Pat. No. 10,016,137), U.S. patent application Ser. No. 15/853,538, entitled "Systems and Methods For Quasi-Ballistic Photon Optical Coherence Tomography In Diffusive Scattering Media Using a Lock-In Camera" (now U.S. Pat. No. 10,219,700), U.S. patent application Ser. No. 16/266,818, entitled "Ultrasound Modulating Optical Tomography Using Reduced Laser Pulse Duration," U.S. patent application Ser. No. 16/299,067, entitled "Non-Invasive Optical Detection Systems and Methods in Highly Scattering Medium," U.S. patent application Ser. No. 16/379,090, entitled "Non-Invasive Frequency Domain Optical Spectroscopy For Neural Decoding," U.S. patent application Ser. No. 16/382,461, entitled "Non-Invasive Optical Detection System and Method," U.S. patent application Ser. No. 16/392,963, entitled "Interferometric Frequency-Swept Source And Detector In A Photonic Integrated Circuit," U.S. patent application Ser. No. 16/392,973, entitled "Non-Invasive Measurement System and Method Using Single-Shot Spectral-Domain Interferometric Near-Infrared Spectroscopy Based On Orthogonal Dispersion, U.S. patent application Ser. No. 16/393,002, entitled "Non-Invasive Optical Detection System and Method Of Multiple-Scattered Light With Swept Source Illumination," U.S. patent application Ser. No. 16/385,265, entitled "Non-Invasive Optical Measurement System and Method for Neural Decoding," U.S. patent application Ser. No. 16/533,133, entitled "Time-Of-Flight Optical Measurement And Decoding Of Fast-Optical Signals," U.S. patent application Ser. No. 16/565,326, entitled "Detection Of Fast-Neural Signal Using Depth-Resolved Spectroscopy," U.S. patent application Ser. No. 16/226,625, entitled "Spatial and Temporal-Based Diffusive Correlation Spectroscopy Systems and Methods," U.S. Provisional Patent Application Ser. No. 62/772,584, entitled "Diffuse Correlation Spectroscopy Measurement Systems and Methods," U.S. patent application Ser. No. 16/432,793, entitled "Non-Invasive Measurement Systems with Single-Photon Counting Camera," U.S. Provisional Patent Application Ser. No. 62/855,360, entitled "Interferometric Parallel Detection Using Digital Rectification and Integration", U.S. Provisional Patent Application Ser. No. 62/855,380, entitled "Interferometric Parallel Detection Using Analog Data Compression," U.S. Provisional Patent Application Ser. No. 62/855,405, entitled "Partially Balanced Interferometric Parallel Detection," U.S. Non-Provisional patent application Ser. No. 16/051,462, entitled "Fast-Gated Photodetector Architecture Comprising Dual Voltage Sources with a Switch Configuration" (now U.S. Pat. No. 10,158,038), U.S. patent application Ser. No. 16/202,771, entitled "Non-Invasive Wearable Brain Interface Systems Including a Headgear and a Plurality of Self-Contained Photodetector Units Configured to Removably Attach to the Headgear" (now U.S. Pat. No. 10,340, 408), U.S. patent application Ser. No. 16/283,730, entitled "Stacked Photodetector Assemblies" (now U.S. Pat. No. 10,515,993), U.S. patent application Ser. No. 16/544,850, entitled "Wearable Systems with Stacked Photodetector Assemblies," U.S. Provisional Patent Application Ser. No. 62/880,025, entitled "Photodetector Architectures for Time-Correlated Single Photon Counting," U.S. Provisional Patent Application Ser. No. 62/889,999, entitled "Photodetector Architectures for Efficient Fast-Gating," and U.S. Provisional Patent Application Ser. No. 62/906,620, entitled "Photodetector Systems with Low-Power Time-To-Digital Converter Architectures," which are all expressly incorporated herein by reference.

Furthermore, alternative embodiments of the neural activity detection system may use a non-optically-based modality to obtain neural activity information, such as magnetically-based modalities to obtain neural activity information, e.g., those described in U.S. patent application Ser. No. 16,428, 871, entitled "Magnetic Field Measurement Systems and Methods of Making and Using," U.S. patent application Ser. No. 16/418,478, entitled "Magnetic Field Measurement System and Method of Using Variable Dynamic Range Optical Magnetometers", U.S. patent application Ser. No. 16/418, 500, entitled, "Integrated Gas Cell and Optical Components for Atomic Magnetometry and Methods for Making and Using," U.S. patent application Ser. No. 16/457,655, entitled "Magnetic Field Shaping Components for Magnetic Field Measurement Systems and Methods for Making and Using," U.S. patent application Ser. No. 16/213,980, entitled "Systems and Methods Including Multi-Mode Operation of Optically Pumped Magnetometer(S)," U.S. patent application Ser. No. 16/456,975, entitled "Dynamic Magnetic Shielding and Beamforming Using Ferrofluid for Compact Magnetoencephalography (MEG)," U.S. patent application Ser. No. 16/752,393, entitled "Neural Feedback Loop Filters for Enhanced Dynamic Range Magnetoencephalography (MEG) Systems and Methods," U.S. patent application Ser. No. 16/741,593, entitled "Magnetic Field Measurement System with Amplitude-Selective Magnetic Shield," U.S. Provisional Patent Application Ser. No. 62/858,636, entitled "Integrated Magnetometer Arrays for Magnetoencephalography (MEG) Detection Systems and Methods," U.S. Provisional Patent Application Ser. No. 62/836,421, entitled "Systems and Methods for Suppression of Non-Neural Interferences in Magnetoencephalography (MEG) Measurements," U.S. Provisional Patent Application Ser. No. 62/842,818 entitled "Active Shield Arrays for Magnetoencephalography (MEG)," U.S. Provisional Patent Application Ser. No. 62/926,032 entitled "Systems and Methods for Multiplexed or Interleaved Operation of Magnetometers," U.S. Provisional Patent Application Ser. No. 62/896,929 entitled "Systems and Methods having an Optical Magnetometer Array with Beam Splitters," and U.S. Provisional Patent Application Ser. No. 62/960,548 entitled "Methods and Systems for Fast Field Zeroing for Magnetoencephalography (MEG)," which are all expressly incorporated herein by reference.

Referring now to FIG. 1, one embodiment of a neural activity detection system 10 constructed in accordance with the present inventions will be described. The neural activity detection system 10 is configured for measuring neural activity in the brain 14 of a user 12, generating commands CMD in response to the measured neural activity information, and sending the commands CMD to an external device 16 in the context of a BCI. To this end, the neural activity detection system 10 generally comprises a signal acquisition module 20, a phase-locked loop (PLL) component 22, a frequency computation component (and in this case, a heart rate (HR) computation component) 24, a periodic artifact cancellation component (and in this case, a cardiac artifact cancellation component) 26, and a signal processor 30.

Figure 2:
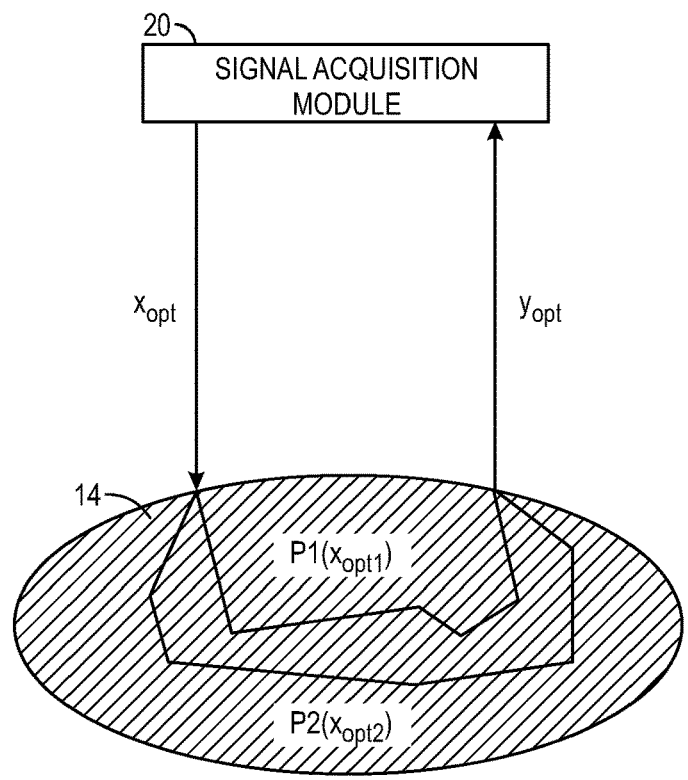
FIG. 2 is a block diagram of a signal acquisition module of the neural activity detection system of FIG. 1.

The signal acquisition unit 20 is configured for optically acquiring a signal y from a brain 14 of a user 12, and in this case, signal light $y_{opt}$, from the brain 14 of the user 12. For example, with further reference to FIG. 2, the signal acquisition unit 20 may be configured for generating and delivering sample light $x_{opt}$ into the brain 14 of the user 12. The sample light $x_{opt}$ scatters diffusively through the brain 14, such that the sample light $x_{opt}$ travels along a bundle of different optical paths P. For purposes of brevity, only a first sample light portion $x_{opt1}$ traveling along a relatively long path $P_1$, and a second sample light portion $x_{opt2}$ traveling along a relatively short path $P_2$, are illustrated, although it should be appreciated that the diffused sample light $x_{opt}$ will travel along many more paths P through the brain 14. After scatting diffusively through the brain 14, the sample light $x_{opt}$ exits the brain 14 as signal light $y_{opt}$, which is detected by the signal acquisition unit 20. Significantly, any physiological activity in the brain 14 will change an optical property (e.g., scattering or absorption) of tissue within the brain 14, and thus, the sample light $x_{opt}$ traveling diffusively through the brain 14, and thus the signal light $y_{opt}$ exiting the brain 14 and detected by the signal acquisition unit 20, will be characterized by the optical property changes in the tissue of the brain 14. It should be appreciated that, although not all of the sample light $x_{opt}$ from which the signal light $y_{opt}$ is derived passes through the brain 14 and is detected, it is only important that at least some of the signal light $y_{opt}$ exiting the brain 14 be detected.

In the illustrated embodiment, the wavelength of the sample light $x_{opt}$, and thus the signal light $y_{opt}$, is in the near-infrared spectrum (e.g., in the range of 650 nm to 750 nm) in accordance with functional infrared spectroscopy (fNIRS), such that the sample light $x_{opt}$ has maximum sensitivity to hemodynamic changes in the brain 14. Notwithstanding the foregoing, it is preferred that the optical wavelength of the sample light $x_{opt}$ be selected to maximize sensitivity to the specific physiological activity of interest. For example, in the preferred case where the physiological activity of interest is the presence of a fast-optical signal, an optical wavelength greater than 850 nm may be used for the sample light $x_{opt}$. Optionally, an optical wavelength equal to or greater 1000 nm may be used for the sample light $x_{opt}$ to maximize penetration. The sample light $x_{opt}$ may be close to monochromatic in nature, comprising approximately a single-wavelength light, or the sample light $x_{opt}$ may have multiple wavelengths (e.g., white light or ultrashort pulse). In some variations, the sample light $x_{opt}$ may have a broad optical spectrum or may have a narrow optical spectrum that is then rapidly swept (e.g., changed over time) to functionally mimic or create an effective broad optical spectrum. Multiple optical wavelengths can be used for the sample light $x_{opt}$ to allow different physiological activities to be distinguished from each other. For example, sample light $x_{opt}$ having two optical wavelengths of 700 nm and 900 nm can be respectively used to resolve hemo-dynamic changes and fast-optical signals. Alternatively, the wavelength of the sample light $x_{opt}$ may be selected to maximize detector sensitivity in the signal acquisition unit 20.

Although the signal acquisition unit 20, for purposes of brevity, is described herein as acquiring an signal light $y_{opt}$ from the brain 14 by using a single fixed source-detector arrangement that emits sample light $x_{opt}$ at a single point into the brain 14, and detects signal light $y_{opt}$ from the brain 14 at a single point, in a practical implementation capable of localizing hemodynamic changes, and thus neural activity, in a plane along the surface of the brain 14, variations of the signal acquisition unit 20 may utilize more complex source-detector arrangements (e.g., single-source multi-detector, multi-source single-detector, or multi-source multi-detector) to simultaneously emit sample light $x_{opt}$ at multiple points into the brain 14 and/or detect signal light $y_{opt}$ from the brain 14 at multiple points, or may utilize a movable source-detector arrangement to sequentially emit sample light $x_{opt}$ at multiple points into the brain 14 and/or detect signal light $y_{opt}$ from the brain 14 at multiple points, as described in U.S. patent application Ser. No. 16/379,090, entitled "Frequency Domain Optical Spectroscopy For Neural Decoding," and U.S. Provisional patent application Ser. No. 16/392,963, entitled "Interferometric Frequency-Swept Source and Detector in a Photonic Integrated Circuit," which are expressly incorporated herein by reference. Thus, in a practical implementation, the neural activity detection system 10 may detect and localize neural activity in the brain 14 in at least two dimensions, represented as an x-y plane spanning the surface of the brain 14.

Figure 3A:
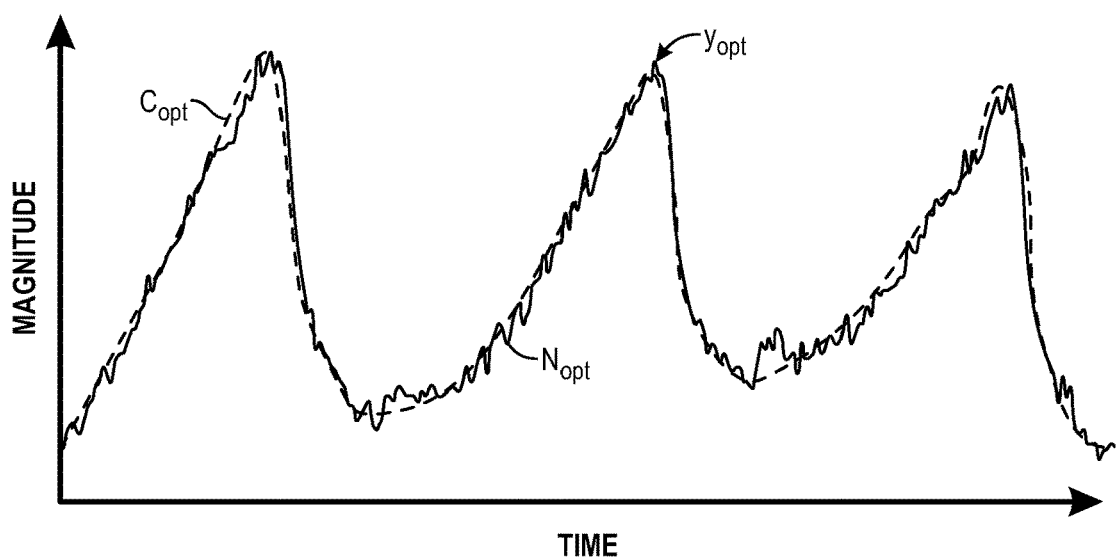
FIG. 3A is a diagram of an exemplary optical signal acquired from a brain of a user, particularly showing a neural-encoded component and a cardiac artifact component.
Figure 4A:
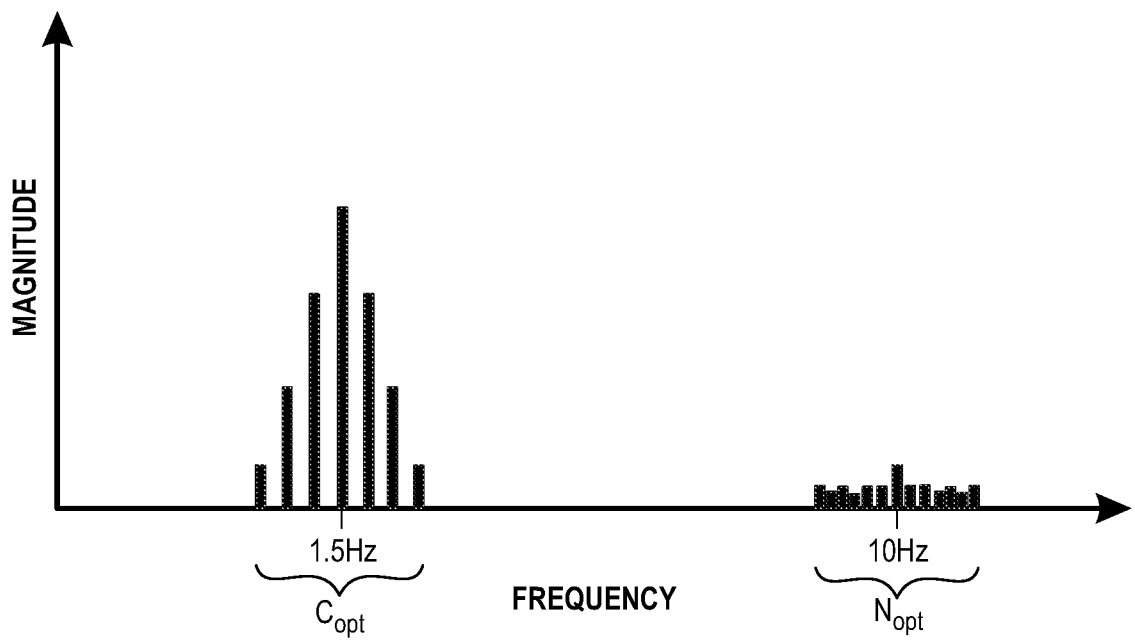
FIG. 4A is a diagram of an exemplary frequency spectrum of the acquired electrical signal of FIG. 3B.

Significantly, as illustrated in FIG. 3A, the signal light $y_{opt}$ acquired by the signal acquisition unit 20 contains an optical physiological-encoded component $N_{opt}$, and in particular, an optical neurological-encoded component (i.e., light representative of a physiological activity indicative of neural activity, and in this case, hemodynamic changes), as well as an optical periodic artifact component, and in particular, an optical cardiac artifact component $C_{opt}$. The optical cardiac artifact component $C_{opt}$ has a strong oscillation in a range that masks, and in fact dominates, the much smaller optical neurological-encoded component $N_{opt}$, which can be best characterized as a small ripple on the optical cardiac artifact component $C_{opt}$. For the purposes of this specification, a dominating periodic artifact component is any periodic artifact component that repeats in a uniform or non-uniform recurrent fashion and has a highest magnitude frequency component that is greater than the highest magnitude frequency component of the physiological-encoded component of interest in an acquired signal. For example, as illustrated in FIG. 4A, in an exemplary acquired signal light $y_{opt}$, the highest magnitude frequency component of an optical cardiac artifact component $C_{opt}$ is 1.5 Hz, while the highest magnitude frequency component of the neural-encoded component $N_{opt}$ is at 10 Hz. The highest magnitude frequency component of the optical cardiac artifact component $C_{opt}$ is significantly greater than the magnitude frequency component of the neural-encoded component $N_{opt}$.

Figure 3B:
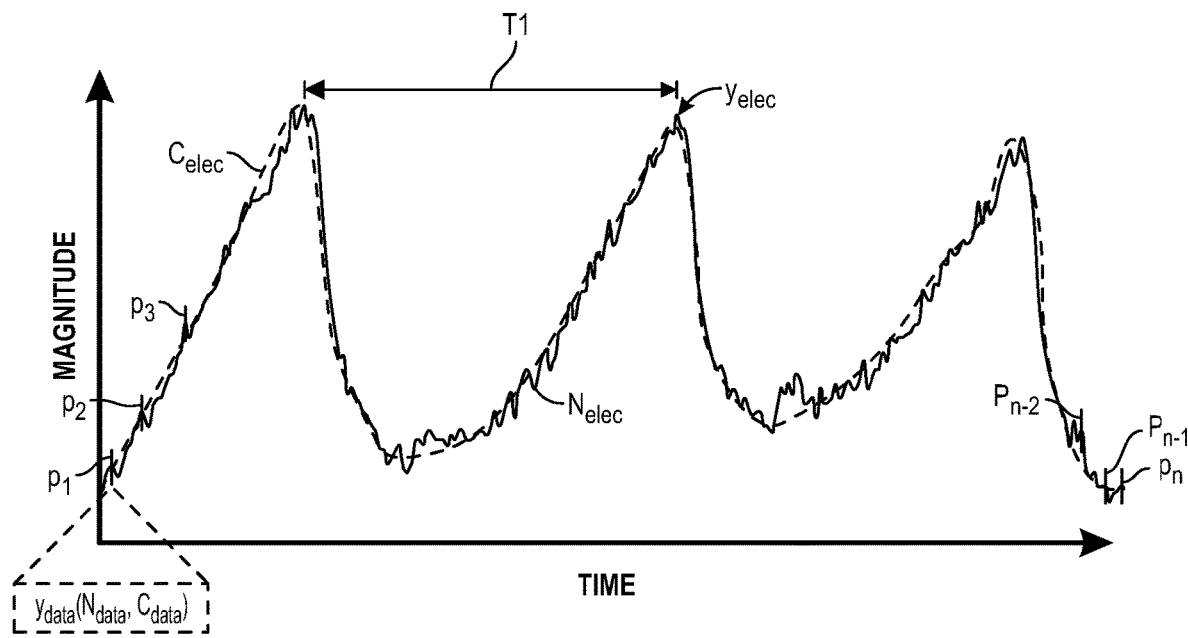
FIG. 3B is a diagram of an exemplary acquired electrical signal transformed from the optical signal of FIG. 3A.

In the illustrated embodiment, the signal acquisition unit 20 is configured for transforming the acquired signal light $y_{opt}$ into an acquired electrical signal $y_{elec}$, which will have a neurological-encoded component $N_{elec}$ and a cardiac artifact component $C_{elec}$ respectively identical to the neurological-encoded component $N_{opt}$ and cardiac artifact component $C_{opt}$ of the acquired signal light $y_{opt}$, as shown in FIG. 3B. In the illustrated embodiment, the signal acquisition unit 20 is further configured for digitally sampling the acquired electrical signal $y_{elec}$ at sample points $p_1$-$p_n$ and outputting a time-series of acquired data samples $y_{data}$ on an output 39 (shown in FIG. 1), each data sample $y_{data}$ having a neurological-encoded component $N_{data}$ and a cardiac artifact component $C_{data}$ respectively corresponding to the neurological-encoded component $N_{elec}$ and the cardiac artifact component $C_{elec}$ in the acquired electrical signal $y_{elec}$ acquired from the brain 14. It is preferred that the rate at which acquired electrical signal $y_{elec}$ is sampled be faster than the hemodynamic changes that occur in response to neural activity in the brain 14, such that these hemodynamic changes can be detected in the in the artifact-reduced electrical signal $y'_{elec}$ (shown in FIG. 3C) from which neural activity in the brain 14 of the user 12 will be derived, as will be described in further detail below.

Figure 5:
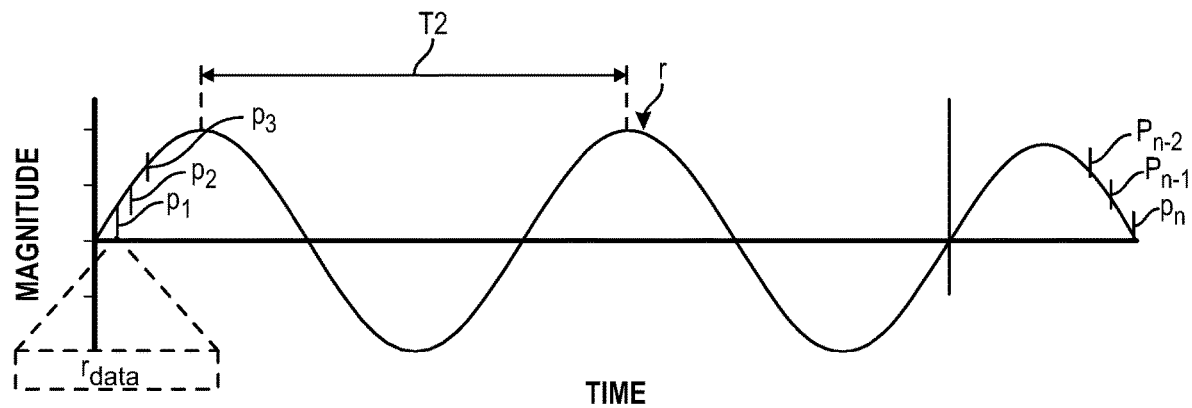
FIG. 5 is a diagram of an exemplary periodic reference signal generated by a phase-locked loop (PLL) component of the neural activity detection system of FIG. 1, wherein the periodic reference signal has a phase representing an estimated phase of the acquired electrical signal of FIG. 3B.

Referring back to FIG. 1, the phase-locked loop (PLL) component 22 is configured for tracking the phase of the cardiac artifact component $C_{elec}$ in the acquired electrical signal $y_{elec}$, and thus, the phase of the cardiac artifact component $C_{elec}$ in the acquired electrical signal $y_{elec}$. In particular, the PLL component 22 outputs a periodic reference signal r (defined by a time-series of reference data samples $r_{data}$), as shown in FIG. 5. The periodic signal r has a phase that is related to the phase of the narrow-band sine wave (i.e., the highest-magnitude frequency component) in the acquired electrical signal $y_{elec}$, and thus, correlated to the phase of the cardiac artifact component $C_{elec}$ in the acquired electrical signal $y_{elec}$. As illustrated in FIG. 5, the periodic reference signal r takes the form of a clean sine wave having a frequency that may vary in accordance with the variation in the frequency of the HR of the user 12, and thus, the cardiac artifact component $C_{elec}$ in the acquired electrical signal $y_{elec}$.

The PLL component 22 learns and updates the phase of the periodic reference signal r that best matches the actual phase of the cardiac artifact component $C_{elec}$ in the acquired electrical signal $y_{elec}$. Thus, the phase of the periodic reference signal r is an estimation, and thus a representation, of the estimated phase of the cardiac artifact component $C_{elec}$ in the acquired electrical signal $y_{elec}$.

In the embodiment illustrated in FIG. 1, the PLL component 22 comprises a phase comparator 32 and a variable frequency oscillator 34 (in this case, a voltage-controlled oscillator (VCO) arranged in a closed feedback loop. The phase comparator 32 is configured for computing the difference between the phase of the highest-magnitude frequency component in the acquired electrical signal $y_{elec}$ (assumed to be the frequency of the cardiac artifact component $C_{elec}$) and the phase of the periodic reference signal r, and adjusting the frequency of the periodic reference signal r subsequently output by the VCO 34 in an effort to match the phases of the cardiac artifact component $C_{elect}$ and the periodic reference signal r. Maintaining the respective phases of the cardiac artifact component $C_{elec}$ of the acquired electrical signal $y_{elec}$ and the periodic reference signal r in lock-step implies that the frequency of the cardiac artifact component $C_{elec}$ and the frequency of the periodic reference signal r will likewise be in lock-step.

To this end, the phase comparator 32 receives the acquired electrical signal $y_{elec}$ (in this case, the acquired data samples $y_{data}$) from the signal acquisition module 20 at a first input 40a and the periodic reference signal r (in this case, the reference data samples $r_{data}$) from the VCO 34 at a second input 40b, computes the difference between the phases of cardiac artifact component $C_{elec}$ of the acquired electrical signal $y_{elec}$ and the periodic reference signal r, and generates and outputs a phase error signal ep (defined by phase error data samples $ep_{data}$) (shown in FIG. 6) on an output 42 representative of the computed difference between the actual phase of the cardiac artifact component $C_{elec}$ of the acquired electrical signal $y_{elec}$ and the phase of the periodic reference signal r (which represents the estimate of the phase of the cardiac artifact component $C_{elec}$ of the acquired electrical signal $y_{elec}$). In the illustrated embodiment, the voltage magnitude of the phase error signal ep is proportional to the difference between the phases of cardiac artifact component $C_{elec}$ of the acquired electrical signal $y_{elec}$ and the periodic reference signal r.

Figure 6:
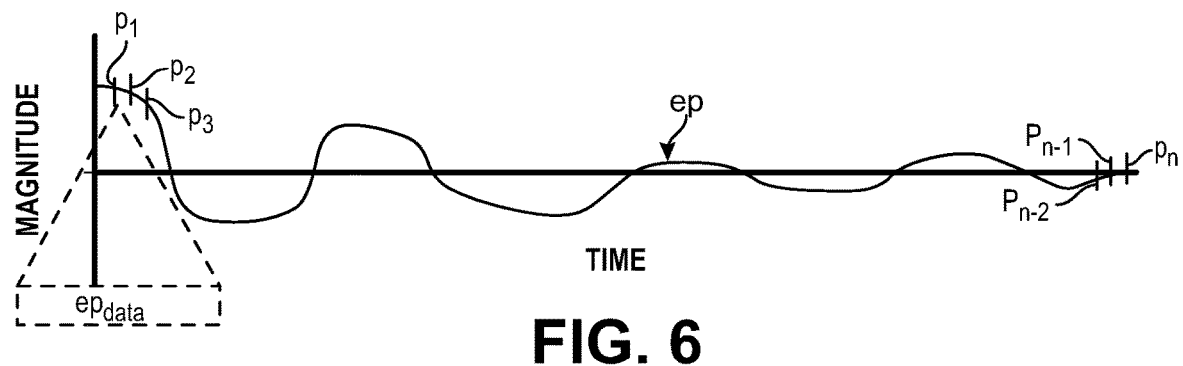
FIG. 6 is a diagram of an exemplary phase error signal used by the PLL component of the neural activity detection system of FIG. 1 to update the phase of the periodic reference signal.

The VCO 34 receives the phase error signal ep (in this case, the phase error data samples $ep_{data}$) on an input 44, and generates and outputs the periodic reference signal r on an output 46 in accordance with the voltage magnitude of the phase error signal ep. That is, the frequency of the periodic reference signal r will be proportional to the magnitude voltage of the phase error signal ep, thereby adjusting the phase of the periodic reference signal r. Since this periodic reference signal r is fed back, as the estimated phase of the acquired electrical signal $y_{elec}$, into the phase comparator 32 via the second input 40b, wherein it is subtracted from the actual phase of the cardiac artifact component $C_{elec}$ of the acquired electrical signal $y_{elec}$ input into the phase comparator 32 via the first input 40a, the PLL component 22 operates to minimize the phase error signal ep (i.e., the difference in the phase of the periodic reference signal r (i.e., the estimated phase of the cardiac artifact component $C_{elec}$ of the acquired electrical signal $y_{elec}$ output by the VCO 34 at that the output 46) and the actual phase of the cardiac artifact component $C_{elec}$ of the acquired electrical signal $y_{elec}$ observed by and input into the PLL component 22 via the first input 40a. For example, as illustrated in FIG. 6, the phase error signal $e_p$ optimally converges to a magnitude close to zero, although the magnitude of the phase error signal ep may periodically diverge away from zero as the HR of the user 12 varies.

As such, the phase of the periodic reference signal r (i.e., the estimated phase of the cardiac artifact component $C_{elec}$ of the acquired electrical signal $y_{elec}$) will be in lock step with the actual phase of the cardiac artifact component $C_{elec}$ of the acquired electrical signal $y_{elec}$, thereby enabling the PLL component 22 to track the phase (and frequency) of the phase of the cardiac artifact component $C_{elec}$ of the acquired electrical signal $y_{elec}$. For example, the temporal distance T1 between the peaks of the acquired electrical signal $y_{elec}$ in FIG. 3B may be approximately equal to the temporal distance T2 between the peaks of the periodic reference signal r in FIG. 5, indicating that the frequencies and phases of the cardiac artifact component $C_{elec}$ in the acquired electrical signal $y_{elec}$ and the periodic reference signal r are in lock-step with each other.

Significantly, the PLL component 22 is capable of tracking the phase, and thus frequency, of the estimated phase of the cardiac artifact component $C_{elec}$ of the acquired electrical signal $y_{elec}$ on a sample-by-sample basis; i.e., acquired data samples $y_{data}$ need not be accumulated or buffered in a batch mode for the PLL component 22 to track the phase and frequency of the cardiac artifact component $C_{elec}$ of the acquired electrical signal $y_{elec}$.

Because the periodic reference signal r takes the form of a clean sine wave with a known (but varying) frequency, the heart rate (HR) computation component 24 is configured for deriving the HR of the user 12 from the periodic reference signal r on a continuous basis. To this end, the HR computation component 24 receives, via an input 48, the periodic reference signal r (in this case, the reference data samples $r_{data}$) from the PLL component 22, and derives and outputs the frequency of the cardiac artifact c (i.e., HR) of the user 12 on an output 50. In one embodiment, the HR computation component 24 estimates the HR of the user 12 by computing the first derivative of the phase of the periodic reference signal r (i.e., the estimated phase of the cardiac artifact component $C_{elec}$ of the acquired electrical signal $y_{elec}$). In another embodiment, the HR computation component 24 estimates the HR of the user 12 by identifying adjacent peaks in the periodic reference signal r, and computing the inverse of the time difference between the adjacent peaks.

Figure 3C:
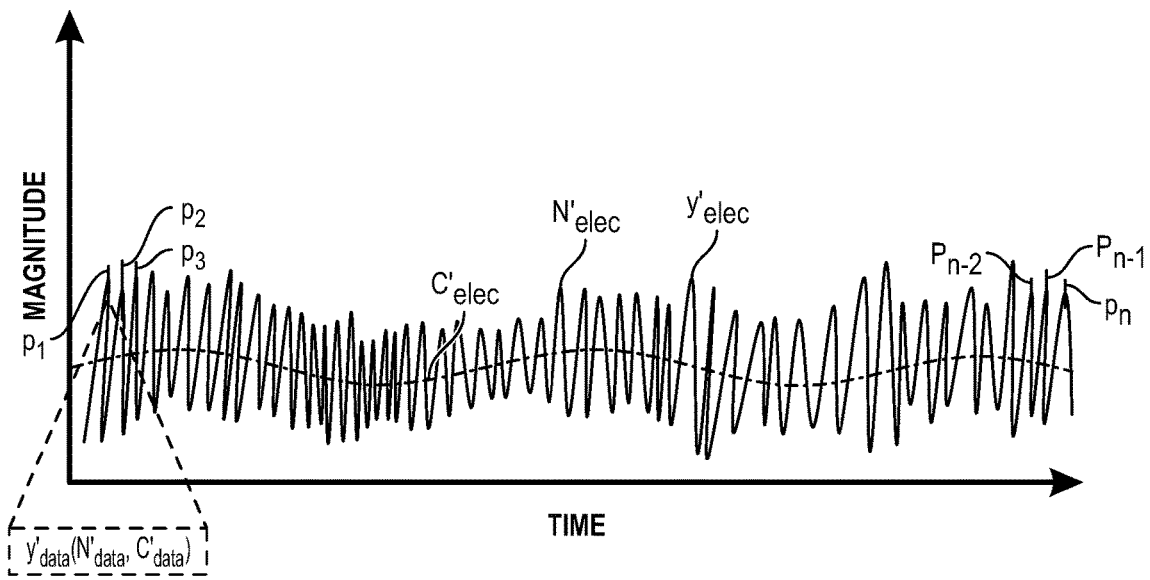
FIG. 3C is a diagram of an exemplary reduced-artifact signal yielded by the neural activity system of FIG. 1 after removing a cardiac artifact component from the acquired electrical signal of FIG. 3B.

The neural activity detection system 10 may use the periodic reference signal r output by the PLL component 22, which is correlated to the cardiac artifact component $C_{elec}$ in the acquired electrical signal $y_{elec}$, to remove the cardiac artifact component $C_{elec}$ from the acquired electrical signal $y_{elec}$, thereby yielding a reduced-artifact electrical signal $y'_{elec}$ in the form of clean data samples $y'_{data}$. As illustrated in FIG. 3C, the reduced-artifact electrical signal y' has a neurological-encoded component N' (defined by neurological-encoded data samples $N'_{data}$) that dominates the cardiac artifact component C' (defined by cardiac artifact data samples $C'_{data}$).

Figure 4B:
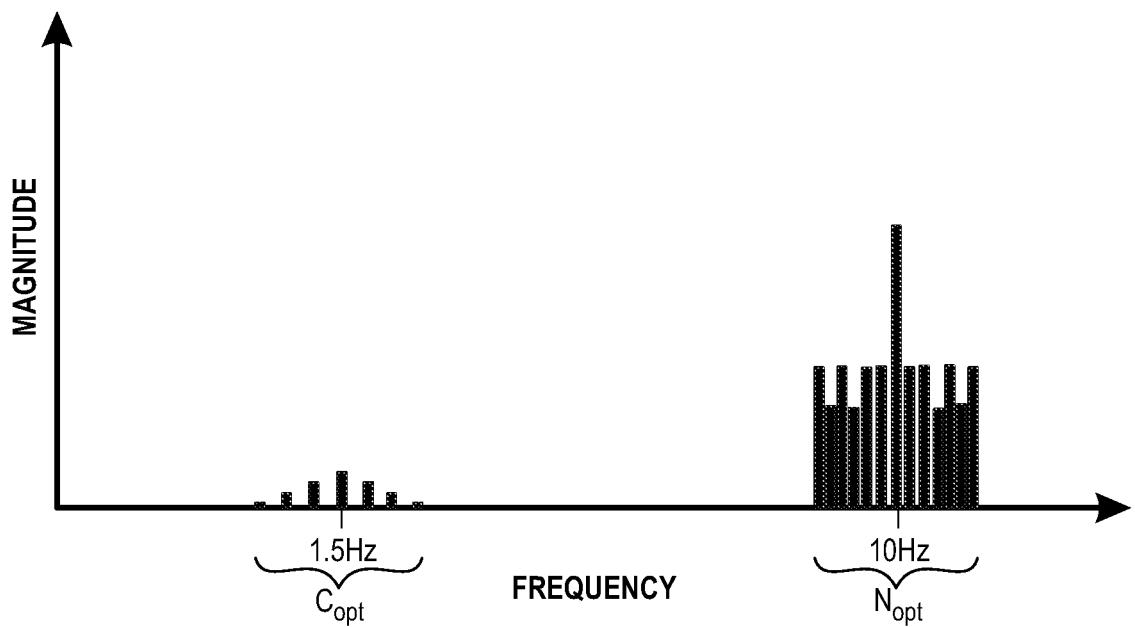
FIG. 4B is a diagram of an exemplary frequency spectrum of the reduced-artifact signal of FIG. 3C.

Preferably, the cardiac artifact component C is substantially eliminated from the acquired electrical signal $y_{elec}$, which for the purposes of this specification, means that the signal-to-noise ratio of the reduced-artifact electrical signal $y'_{elec}$ (i.e., the ratio of the power of the neurological-encoded component N over the power of the cardiac artifact C of the reduced-artifact electrical signal $y'_{elec}$) is 10 db higher than the signal-to-noise ratio of the acquired electrical signal $y_{elec}$ (i.e., the ratio of the power of the neurological-encoded component $N_{elec}$ over the power of the cardiac artifact $C_{elec}$ of the acquired electrical signal $y_{elec}$). For example, as illustrated in FIG. 4B, in an exemplary reduced-artifact electrical signal $y'_{elec}$, the highest magnitude frequency component of the optical cardiac artifact component $C_{opt}$ is significantly less than the magnitude frequency component of the neural-encoded component $N_{opt}$.

Figure 7:
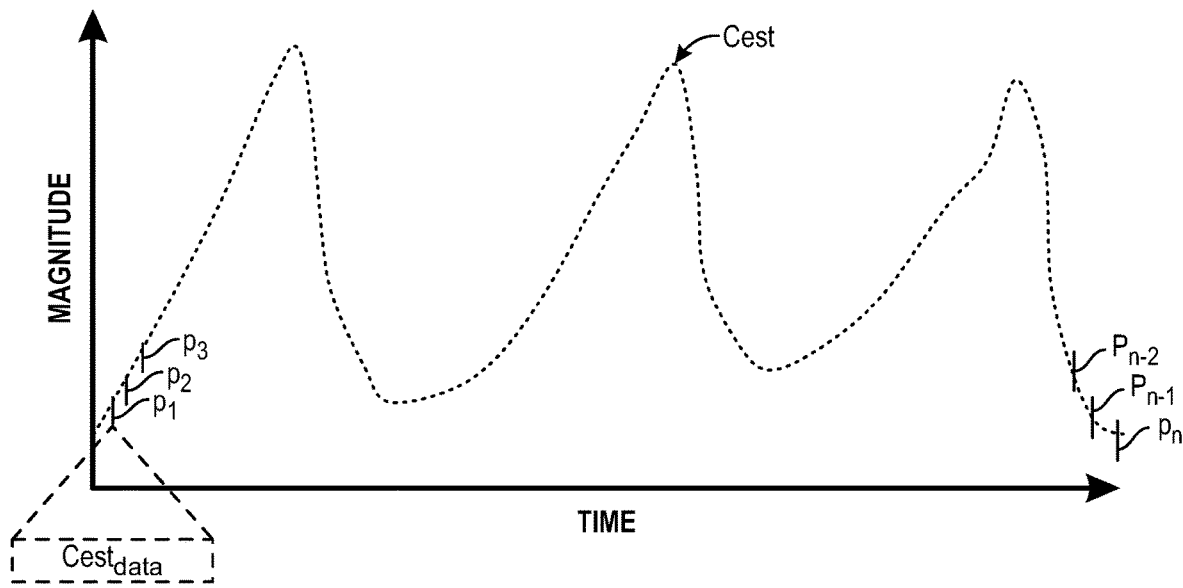
FIG. 7 is a diagram of an exemplary estimated cardiac artifact cancellation component generated by the artifact cancellation component of the neural activity detection system of FIG. 1.

To this end, the artifact cancellation component 26 is configured for filtering the cardiac artifact component $C_{elec}$ from the acquired signal light $y_{opt}$ in accordance with a variable transfer function based on the periodic reference signal r, thereby yielding the reduced-artifact electrical signal $y'_{elec}$. Notably, because the periodic reference signal r is not mapped to the acquired electrical signal $y_{elec}$ (i.e., the periodic signal r is not a properly scaled and offset version of the cardiac artifact component $C_{elec}$ of the acquired electrical signal $y_{elec}$), it cannot be simply subtracted from the acquired electrical signal $y_{elec}$ to yield the reduced-artifact electrical signal $y'_{elec}$. The artifact cancellation component 26 is configured for mapping the periodic reference signal r to the acquired electrical signal $y_{elec}$. Such mapping has a scale parameter (gain) and offset, thereby yielding an estimated cardiac artifact Cest in the form of estimated cardiac artifact data samples $Cest_{data}$ (illustrated in FIG. 7) that is properly scaled and offset to the cardiac artifact component $C_{elec}$ of the acquired electrical signal $y_{elec}$.

Significantly, the artifact cancellation component 26 is capable of filtering the cardiac artifact component $C_{elec}$ from the acquired electrical signal $y_{elec}$ on a sample-by-sample basis; i.e., the acquired data samples $y_{data}$ need not be accumulated or buffered in a batch mode for the artifact cancellation component 26 to filter the cardiac artifact component $C_{elec}$ from the acquired electrical signal $y_{elec}$. To this end, the artifact cancellation component 26 uses a recursive least squares (RLS) algorithm to map the periodic reference signal r to the acquired electrical signal $y_{elec}$, such that the cardiac artifact component $C_{elec}$ can be smoothly reconstructed from the acquired electrical signal $y_{elec}$, thereby yielding an estimated cardiac artifact Cest without any jumps.

In the embodiment illustrated in FIG. 1, the cardiac artifact cancellation component 26 comprises an adaptive filter 36, a first signal comparator 38, arranged in a closed feedback loop with the adaptive filter 36, and a second signal comparator 40.

Figure 8:
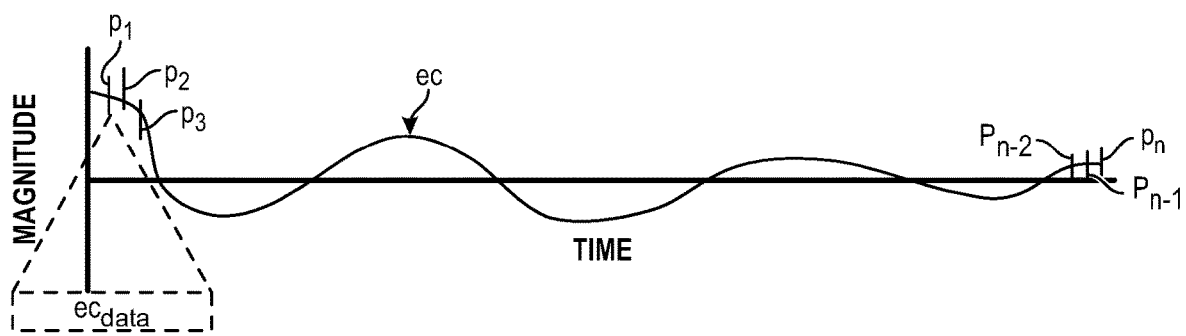
FIG. 8 is a diagram of an exemplary phase error signal used by the cardiac artifact cancellation component of the neural activity detection system of FIG. 1 to update the estimated cardiac artifact cancellation component.

The adaptive filter 36 is configured for filtering the acquired electrical signal $y_{elec}$ in accordance with a linearly variable transfer function that is controlled by variable parameters (e.g., coefficients and/or weights), and generating the estimated cardiac artifact Cest, while the first signal comparator 38 is configured for generating a magnitude error signal ec (defined by magnitude error data samples $ec_{data}$) (shown in FIG. 8) representing the computed difference between the estimated cardiac artifact Cest and the periodic reference signal r), which is then used by the RLS algorithm in the adaptive filter 36 to recursively adjust or update the variable parameters of the transfer function of the adaptive filter 36 in manner that minimizes the magnitude error signal ec on a sample-by-sample basis. For example, as illustrated in FIG. 8, the magnitude error signal ec optimally converges to a magnitude close to zero, although the magnitude of the magnitude error signal ec may periodically diverge away from zero as the HR of the user 12 varies. The adaptive filter 36 attempts to filter the acquired electrical signal $y_{elec}$ into a replica of the cardiac artifact component $C_{elec}$ of the acquired electrical signal $y_{elec}$ by minimizing the magnitude error signal ec. When the magnitude error signal ec is minimized, the output of the adaptive filter 36 is an estimate of the cardiac artifact component $C_{elec}$ of the acquired electrical signal $y_{elec}$ (i.e., the estimated cardiac artifact Cest).

To this end, the first signal comparator 38 receives the periodic reference signal r (in this case, the reference data samples $r_{data}$) from the PLL component 22 on a first input 52a and estimated cardiac artifact Cest (in this case, estimated cardiac artifact data samples $Cest_{data}$) from the adaptive filter 36 on a second input 52b, computes the difference between the magnitude of the estimated cardiac artifact Cest and the magnitude of the periodic reference signal r, and generates and outputs the magnitude error signal e, (in this case, magnitude error data samples $ec_{data}$) on an output 54 representative of the computed difference between the magnitudes of the estimated cardiac artifact Cest and the periodic reference signal r. In the illustrated embodiment, the voltage magnitude of the magnitude error signal ec is proportional to the difference between the magnitudes of the estimated cardiac artifact Cest and the periodic reference signal r.

The adaptive filter 36 receives the acquired electrical signal $y_{elec}$ (in this case, the acquired data samples $y_{data}$) from the signal acquisition module 20 at a first input 56a, and the magnitude error signal ec (in this case, the magnitude error data samples $ec_{data}$) from the first signal comparator 38 on a second input 56b, internally varies the transfer function in accordance with the magnitude error signal ec, filters the cardiac artifact component $C_{elec}$ from the acquired electrical signal $y_{elec}$ in accordance with the varied transfer function, and generates and outputs the estimated cardiac artifact Cest (in this case, estimated cardiac artifact data samples $Cest_{data}$) on an output 58. The estimated cardiac artifact Cest is a properly scaled and offset version of the actual cardiac artifact Celec in the acquired electrical signal $y_{elec}$, such that the estimated cardiac artifact Cest output by the adaptive filter 38 can simply be subtracted from the acquired electrical signal $y_{elec}$ via the second signal comparator 40.

To this end, the second signal comparator 40 receives the acquired electrical signal $y_{elec}$ (in this case, the acquired data samples $y_{data}$) from the signal acquisition module 20 on a first input 60a and the estimated cardiac artifact Cest (in this case, estimated cardiac artifact data samples $Cest_{data}$) from the adaptive filter 36 on a second input 60b, computes the difference between the magnitudes of the acquired electrical signal $y_{elec}$ and the estimated cardiac artifact Cest on a sample-by-sample basis, and outputs the reduced-artifact electrical signal $y'_{elec}$ (in this case, reduced-artifact data samples $y'_{data}$).

It should be appreciated that there are various techniques for using the periodic reference signal r output by the PLL component 22 to remove the cardiac artifact component $C_{elec}$ from the acquired electrical signal $y_{elec}$. For example, with reference to FIG. 9, an alternative embodiment of an artifact cancellation component 26' comprises an adaptive filter 36' and a signal comparator 38' arranged in a closed feedback loop with the adaptive filter 36'.

Figure 9:
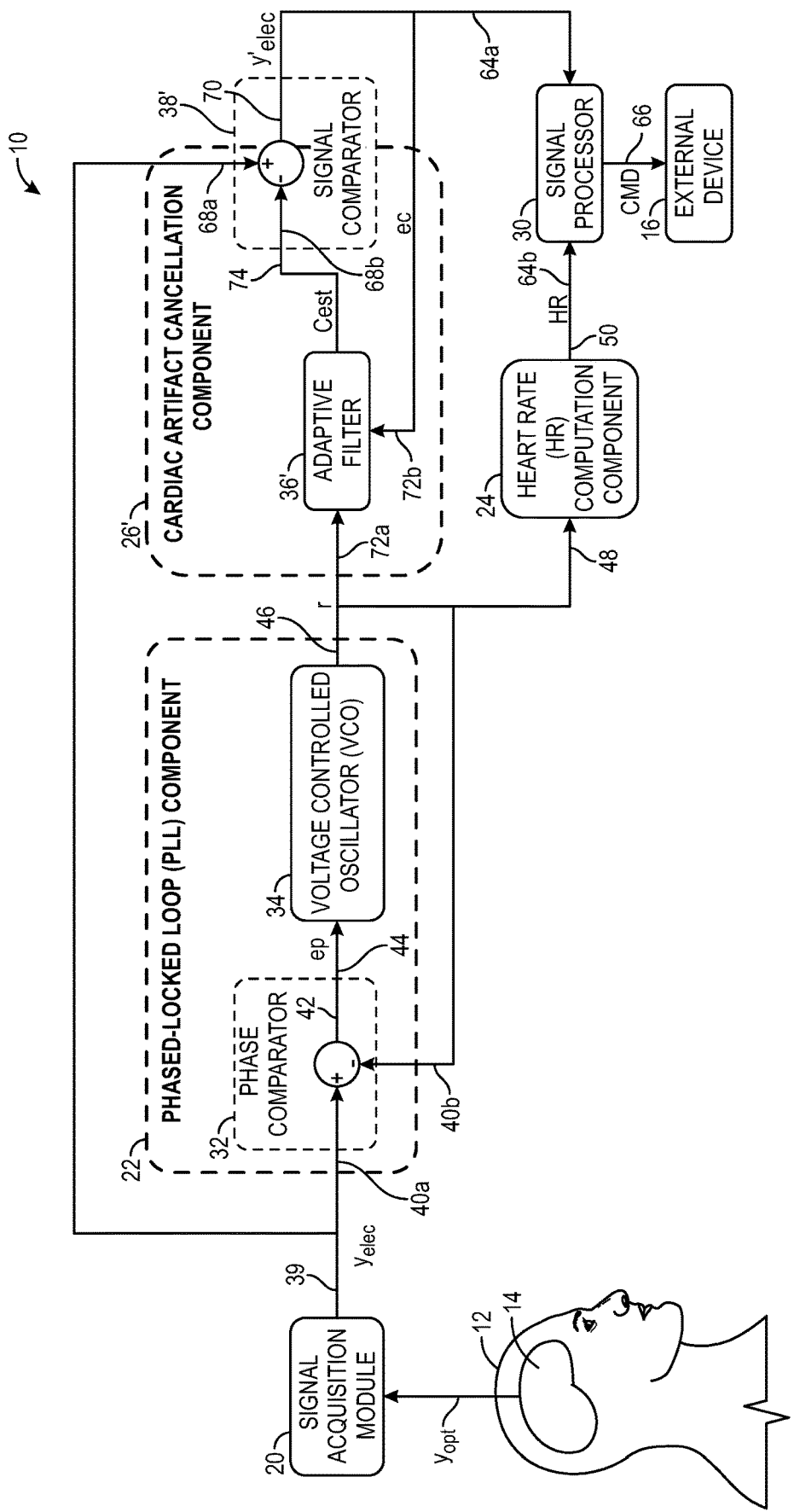
FIG. 9 is a block diagram of a neural activity detection system constructed in accordance with another embodiment of the present inventions.

In the alternative embodiment shown in FIG. 9, instead of filtering the acquired electrical signal $y_{elec}$, the adaptive filter 36' is configured for filtering the periodic reference signal r in accordance with a linearly variable transfer function that is controlled by variable parameters (e.g., coefficients and/or weights), and generating the estimated cardiac artifact Cest, while the signal comparator 38' is configured for generating the magnitude error signal ec (defined by magnitude error data samples $ec_{data}$) representing the computed difference between the estimated cardiac artifact Cest and the acquired electrical signal $y_{elec}$), which is then used by the RLS algorithm in the adaptive filter 36' to recursively adjust or update the variable parameters of the transfer function of the adaptive filter 36' in manner that minimizes the magnitude error signal ec on a sample-by-sample basis. The adaptive filter 36' attempts to filter the periodic reference signal r into a replica of the cardiac artifact component $C_{elec}$ of the acquired electrical signal $y_{elec}$ by minimizing the magnitude error signal ec. When the magnitude error signal ec is minimized, the output of the adaptive filter 36' is an estimate of the cardiac artifact component $C_{elec}$ of the acquired electrical signal $y_{elec}$ (i.e., the estimated cardiac artifact Cest). It should be appreciated that since the magnitude error signal ec represents the computed difference between the estimated cardiac artifact Cest and the acquired electrical signal $y_{elec}$, the magnitude error signal ec is the reduced-artifact signal $y'_{elec}$.

To this end, the signal comparator 38' receives the acquired electrical signal $y_{elec}$ (in this case, the acquired data samples ydata) from the signal acquisition module 20 on a first input 68a and the estimated cardiac artifact Cest (in this case, estimated cardiac artifact data samples $Cest_{data}$) from the adaptive filter 36' on a second input 68b, computes the difference between the magnitude of the estimated cardiac artifact Cest and the magnitude of the periodic reference signal r, and generates and outputs the magnitude error signal e, (in this case, magnitude error data samples $ec_{data}$) on an output 70 representative of the computed difference between the magnitudes of the estimated cardiac artifact Cest and the periodic reference signal r. In the illustrated embodiment, the voltage magnitude of the magnitude error signal ec is proportional to the difference between the magnitudes of the estimated cardiac artifact Cest and the periodic reference signal r.

The adaptive filter 36' receives the periodic reference signal r (in this case, the reference data samples $r_{data}$) from the PLL component 22 at a first input 72a, and the magnitude error signal ec (in this case, the magnitude error data samples $ec_{data}$) from the signal comparator 38' on a second input 72b, internally varies the transfer function in accordance with the magnitude error signal ec, filters the cardiac artifact component $C_{elec}$ from the periodic reference signal r in accordance with the varied transfer function, and generates and outputs the estimated cardiac artifact Cest (in this case, estimated cardiac artifact data samples $Cest_{data}$) on an output 74. The estimated cardiac artifact Cest is a properly scaled and offset version of the actual cardiac artifact Celec in the acquired electrical signal $y_{elec}$, such that the estimated cardiac artifact Cest output by the adaptive filter 36' can simply be subtracted from the acquired electrical signal $y_{elec}$ via the signal comparator 38', as discussed above.

Referring back to FIG. 1, the signal processor 30 is configured for processing, in accordance with a fNIRS technique, the reduced-artifact signal $y'_{elec}$ to determine hemodynamic changes, and thus identify the occurrence, extent of, and location of neural activity, within the cortical structures of the brain 14 of the user 12. The signal processor 30 may optionally be configured for processing the HR of the user 12 for other purposes, such as providing information indicating the existence of neural activity in the sub-cortical structures of the brain 14 of the user 12.

To this end, the signal processor 30 receives the reduced-artifact signal $y'_{elec}$ from the artifact cancellation component 26 (or 26') on a first input 64a, and optionally the HR of the user 12 from the HR computation component 24 on a second input 64b, generates commands CMD based on neural activity information acquired from the reduced-artifact signal $y'_{elec}$ and optionally the HR, and outputs the commands CMD on an output 66 to the external device 16.

Figure 10:
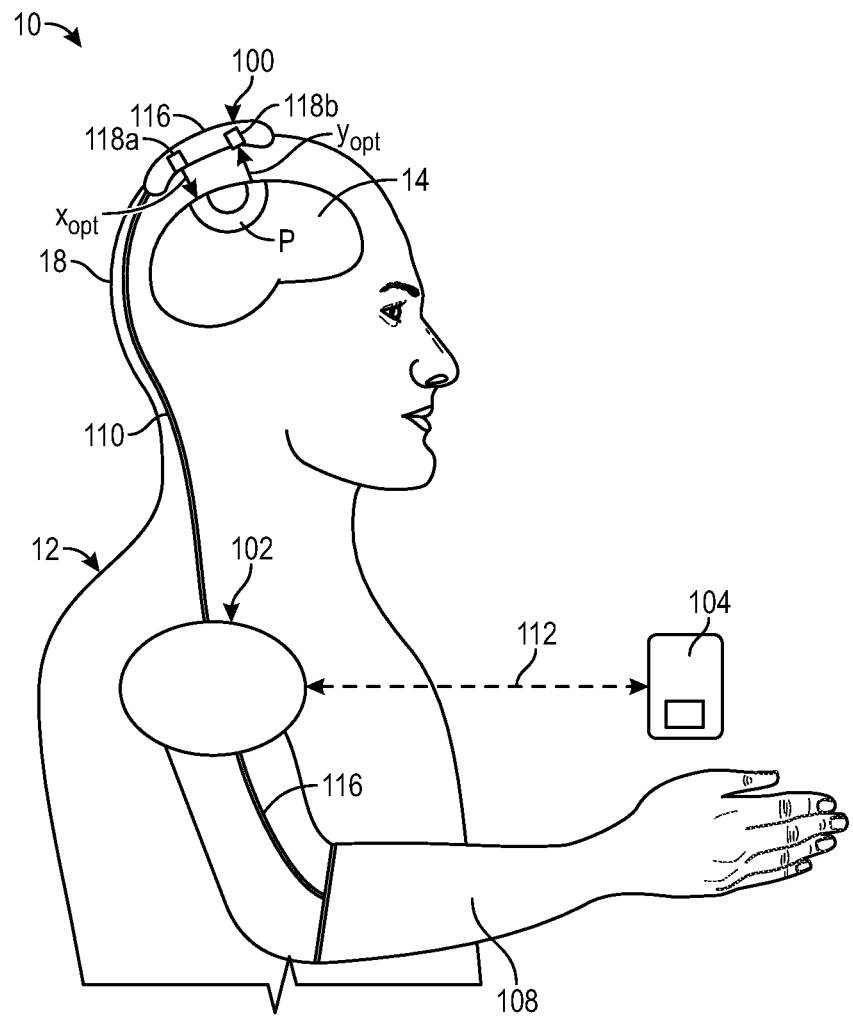
FIG. 10 is a plan view of a physical implementation of the neural activity detection system of FIG. 1.

Referring now to FIG. 10, one physical implementation of the neural activity detection system 10 for use in detecting and localizing neural activity in the brain 14 of a user 12 in the context of a BCI will be described. The neural activity detection system 10 includes a wearable unit 100 that is configured for being applied to the user 12, and in this case, worn on the head 18 of the user 12; an auxiliary head-worn or non-head-worn unit 102 (e.g., worn on the neck, shoulders, chest, or arm) coupled to the wearable unit 100 via a wired connection 110 (e.g., electrical wires); an optional remote processor 104 in communication with the auxiliary unit 102 coupled via a wired connection 112 (e.g., electrical wires), and an external device 108 in communication with the user-wearable auxiliary unit 102 via a wired connection 116. Alternatively, the non-invasive optical detection system 10 may use a non-wired connection (e.g., wireless radio frequency (RF) signals (e.g., Bluetooth, Wifi, cellular, etc.) or optical links (e.g., fiber optic or infrared (IR)) for providing power to or communicating between the respective wearable unit 100 and the auxiliary unit 102, and between the auxiliary unit 102 and the external device 108, and/or a wired connection between the auxiliary unit 102 and the remote processor 104.

The wearable unit 100 comprises a support structure 116 that contains the signal acquisition unit 20, and includes an output port 118a configured for delivering sample light $x_{opt}$ generated by the signal acquisition unit 20 into the brain 14 of the user 12, and an input port 118a configured for receiving signal light $y_{opt}$ from the brain 14 of the user 12 and delivering it to the signal acquisition unit 20. The support structure 116 may be shaped, e.g., have a banana, headband, cap, helmet, beanie, other hat shape, or other shape adjustable and conformable to the head 18, such that the ports 118a, 118b are in close contact with the outer skin of the head 18, and in this case, the scalp of the user 12. In an alternative embodiment, optical fibers (not shown) may be respectively extended from the ports 118a, 118b, thereby freeing up the requirement that the ports 118a, 118b be disposed in close proximity to the surface of the head 18. In any event, an index matching fluid may be used to reduce reflection of the light generated by the wearable unit 100 from the outer skin of the scalp. A strap or belt (not shown) can be used to secure the support structure 116 to the head 18 of the user 12.

In one embodiment, the support structure 116 also contains the PLL component 22, HR computation component 24, and cardiac artifact cancellation component 26 (or 26'). The auxiliary unit 102 contains the signal processor 30 and any control circuitry (not shown) necessary to control the operational functions of the wearable unit 100. Alternatively, any of the PLL component 22, HR computation component 24, and cardiac artifact cancellation component 26 (or 26') may be contained in the auxiliary unit 102, or the signal processor 30 may be contained in the support structure 116. The auxiliary unit 102 may additionally include a power supply (which if head-worn, may take the form of a rechargeable or non-chargeable battery), a control panel with input/output functions, a display, and memory. Alternatively, power may be provided to the auxiliary unit 102 wirelessly (e.g., by induction).

The remote processor 104 may store data from previous sessions, and include a display screen. In response to detecting and localizing neural activity in the brain 14 of the user 12, the signal processor 30 issues and sends commands to the external device 108 to control movement in response in accordance with the deliberate intentions of the user 12, as interpreted by the signal processor 30 from the detected and localized neural activity in the brain 14 of the user 12.

The functionality of the signal acquisition module PLL component 22, HR computation component 24, cardiac artifact cancellation component 26 (or 26'), and signal processor 30 may be implemented using one or more suitable computing devices or digital processors, including, but not limited to, a microcontroller, microprocessor, digital signal processor, graphical processing unit, central processing unit, application specific integrated circuit (ASIC), field programmable gate array (FPGA), and/or programmable logic unit (PLU). Such computing device(s) or digital processors may be associated with non-transitory computer- or processor-readable medium that stores executable logic or instructions and/or data or information, which when executed, perform the functions of these components. The non-transitory computer- or processor-readable medium may be formed as one or more registers, for example of a microprocessor, FPGA, or ASIC, or can be a type of computer-readable media, namely computer-readable storage media, which may include, but is not limited to, RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Figure 11A:
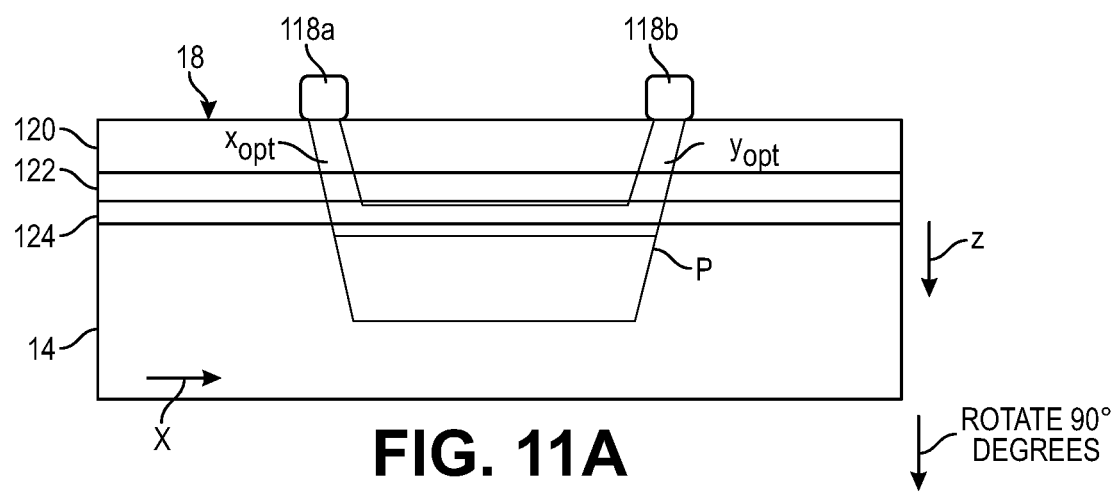
FIG. 11A is one profile view of one arrangement of the output port and input port of the wearable unit of FIG. 10, particularly illustrating the creation of a sample path in the head between the ports.
Figure 11B:
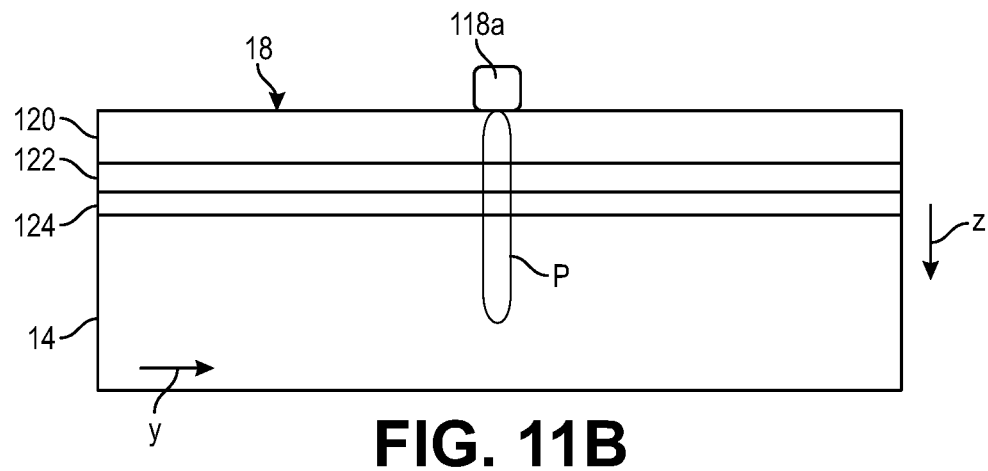
FIG. 11B is another profile view of the arrangement of the output port and input port of the wearable unit of FIG. 10.

As better illustrated in FIGS. 11A and 11B, the wearable unit 100 is configured for being placed adjacent to the head 18 of the user 12 and emitting the sample light $x_{opt}$ into the brain 14, where is scatters, resulting in the neural-encoded signal light $y_{opt}$ that exits the brain 14. In particular, the sample light $x_{opt}$ first passes through the scalp 120, skull 122, and cerebral spinal fluid (CSF) 124 along a relatively straight path, enters the brain 14, then exits in reverse fashion along a relatively straight path through the CSF 124, skull 122, and scalp 120, thereby defining a banana-shaped optical path bundle P. The wearable unit 100 may alternatively, by adding additional output ports 118a and/or input ports 118b, create multiple spatially separated detected optical path bundles P along which the light may propagate to enable x-y spatial localization of the signal light $y_{opt}$. For details discussing wearable units with multiple source-detector pairs are described in U.S. patent application Ser. No. 16/379,090, entitled "Frequency Domain Optical Spectroscopy For Neural Decoding," and U.S. Provisional patent application Ser. No. 16/392,963, entitled "Interferometric Frequency-Swept Source and Detector in a Photonic Integrated Circuit," which are expressly incorporated herein by reference.

For details discussing applications using BCI wearable units are described in U.S. patent application Ser. No. 16,364,338, entitled "Biofeedback for Awareness and Modulation of Mental State Using a Non-Invasive Brain Interface System and Method," U.S. Provisional Patent Application Ser. No. 62/829,124, entitled "Modulation of Mental State of a User Using a Non-Invasive Brain Interface System and Method," U.S. Provisional Patent Application Ser. No. 62/894,578, entitled "Non-Invasive System and Method for Product Formulation Assessment Based on Product-Elicited Brain State Measurements," and U.S. Provisional Patent Application Ser. No. 62/891,128, entitled "Non-Invasive Systems and Methods for the Detection and Modulation of a User's Mental State Through Awareness of Priming Effects," which are expressly incorporated herein by reference.

Figure 12:
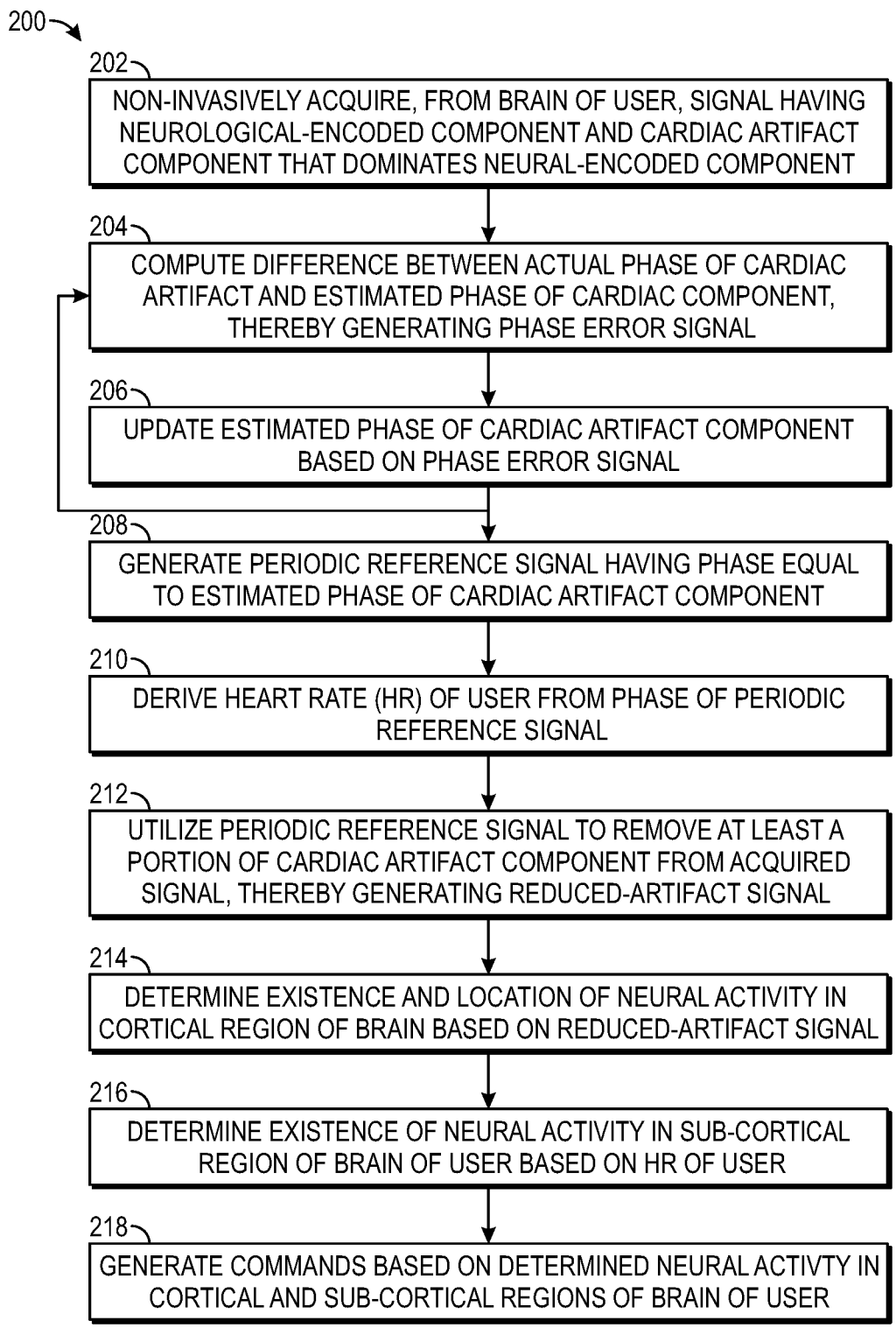
FIG. 12 is a flow diagram illustrating one method used by the neural activity detection system of FIG. 1 to non-invasively determine neural activity in the brain of the user.

Having described the structure and function of the neural activity detection system 10, one particular method 200 performed by the neural activity detection system 10 to non-invasively detect and localize physiological activity (and in this case, neural activity) in an anatomical structure (in this case, the brain 14) of a user 12, and controlling an external device 108, will now be described with respect to FIG. 12.

First, the signal acquisition module 20 non-invasively acquires, from the anatomical structure (and in this case, the brain 14) of the user 12, a signal having a physiological-encoded component (and in particular a neurological-encoded component $N_{opt}$) and a periodic artifact component (and in particular, a cardiac artifact component $C_{opt}$) that dominates the physiological-encoded component) (step 202).

In the illustrated embodiment, the signal acquisition module 20 delivers the sample light $x_{opt}$ into the brain 12 along a detected optical path bundle P, such that the sample light $x_{opt}$ is scattered by the brain 12, resulting in signal light $y_{opt}$ (having a physiological-encoded component (and in particular a neurological-encoded component $N_{opt}$) and a periodic artifact component (and in particular, a cardiac artifact component $C_{opt}$) that dominates the physiological-encoded component) that exits the brain 12, which is then detected by the signal acquisition module 20. In the illustrated embodiment, signal acquisition module 20 acquires the signal light $y_{opt}$ via, e.g., fNIRS, such that the signal light $y_{opt}$ is sensitive to hemodynamic changes in the brain 12 that occur in response to neural activity, although other types of optical modalities, and even non-optical modalities, can be used by the signal acquisition module 20 to acquire a signal from which neural activity in the brain 12 can be derived. The signal acquisition module 20 then transforms the signal light $y_{opt}$ into an acquired electrical signal $y_{elec}$ having a neurological-encoded component $N_{elec}$ and a cardiac artifact component $C_{elec}$, which are replicas of the neurological-encoded component $N_{opt}$ and the cardiac artifact component $C_{opt}$ of the signal light $y_{opt}$. The signal acquisition module 20 then digitizes the acquired electrical signal $y_{elec}$ into acquired data in the form of a time-series of data samples $y_{data}$, each having a neurological-encoded component $N_{data}$ and a cardiac artifact component $C_{data}$ that respectively correspond to neurological-encoded component $N_{elec}$ and a cardiac artifact component $C_{elec}$ of the acquired electrical signal $y_{elec}$, and outputs the data samples $y_{data}$ on the output 39 (shown in FIG. 1).

Next, the PLL component 22 computes a difference between an actual phase of the cardiac artifact component of the acquired signal and an estimated phase of the cardiac artifact component, thereby generating a phase error signal (step 204), updates the estimated phase of the cardiac artifact component of the acquired signal based on the phase error signal (step 206), and generates a periodic reference signal having a phase equal to the estimated phase of the periodic artifact component of the acquired signal (step 208).

In the illustrated embodiment, the PLL component 22 performs the phase error generation and estimated phase updating steps by computing a difference between the phase of the periodic artifact component of the acquired signal and the phase of the periodic reference signal, thereby respectively generating the phase error signal, and varying the frequency of the periodic reference signal in accordance with the phase error signal, thereby varying the phase of the periodic reference signal.

In particular, the phase comparator 32 of the PLL component 22 receives an nth acquired data sample $y_{data}$ from the signal acquisition module 20 at the first input 40a, receives an (nth−1) reference data sample $r_{data}$ from the VCO 34 (as the estimation of the cardiac artifact component $C_{data}$ of the nth acquired data sample $y_{data}$) at the second input 40b, computes the difference between nth acquired data sample $y_{data}$ and the (nth−1) reference data sample $r_{data}$ to determine the difference between the actual and estimated phases of the cardiac artifact component $C_{data}$ of the nth acquired electrical signal $y_{elec}$, and outputs an nth phase error data sample $ep_{data}$ on the output 42. The VCO 34 receives the nth phase error data sample $ep_{data}$ from the phase comparator 32 on the input 44, and generates an nth reference data sample $r_{data}$ on the output 46 having a magnitude in accordance with a frequency defined by the voltage magnitude of the nth phase error data sample $ep_{data}$. That is, the instantaneous frequency of the periodic reference signal r output by the VCO 34 will be proportional to the magnitude voltage of the nth reference data sample $r_{data}$, thereby updating the phase of the periodic reference signal r.

Then, the phase comparator 32 receives an (nth+1) acquired data sample $y_{data}$ from the signal acquisition module 20 at the first input 40, receives the nth reference data sample $r_{data}$ from the VCO 34 (as the estimation of the cardiac artifact component $C_{data}$ of the (nth+1) acquired data sample $y_{data}$) at the second input 40b, computes the difference between (nth+1) acquired data sample $y_{data}$ and the (nth−1) reference data sample $r_{data}$ to determine the difference between the actual and estimated phases of the cardiac artifact component $C_{data}$ of the nth acquired electrical signal $y_{elec}$, and outputs an (nth+1) phase error data sample $ep_{data}$ on the output 42. The VCO 34 receives the (nth+1) phase error data sample $ep_{data}$ from the phase comparator 32 on the input 44, and generates an nth reference data sample $r_{data}$ on the output 46 having a magnitude in accordance with a frequency defined by with the voltage magnitude of the nth phase error data sample $ep_{data}$. This process is repeated for subsequently acquired data samples $y_{data}$.

Next, the HR computation component 24 derives a frequency of the periodic artifact component of the acquired signal, and in particular, the HR of the user 12 from the phase of the periodic reference signal (step 210). In the illustrated embodiment, the HR computation component 24 receives a series of reference data samples $r_{data}$ from the PLL component 22 at the input 48, derives the HR of the user 12 from the reference data samples $r_{data}$ (i.e., the estimated frequency of the cardiac artifact component $C_{elec}$ of the acquired electrical signal $y_{elec}$), and outputs the HR on the output 50.

Next, the cardiac artifact cancellation component 26 (or 26') utilizes the periodic reference signal to remove at least a portion of the cardiac artifact component from the acquired signal, thereby yielding a reduced-artifact signal (step 212). Preferably, the neurological-encoded component dominates the cardiac artifact component in the reduced-artifact signal. More preferably, the cardiac artifact component is substantially eliminated from the reduced-artifact signal.

The cardiac artifact cancellation component 26 illustrated in FIG. 1 computes a difference between a magnitude of an estimated periodic artifact component and a magnitude of the periodic reference signal, thereby generating a magnitude error signal, varies its transfer function in response to the magnitude error signal (e.g., utilizing an RLS algorithm), filters the acquired signal in accordance with the varied transfer function, thereby generating the estimated periodic artifact component, and computes the difference between a magnitude of the acquired signal and a magnitude of the estimated periodic artifact component to yield the reduced-artifact signal.

In particular, the first signal comparator 38 of the cardiac artifact cancellation component 26 receives the (nth−1) reference data sample $r_{data}$ from the PLL component 22 at the first input 52a, receives an nth estimated cardiac artifact data sample $Cest_{data}$ from the adaptive filter 36 at the second input 52b, computes the difference between the magnitude of the (nth−1) reference data sample $r_{data}$ and the magnitude of the (nth−1) estimated cardiac artifact data sample $Cest_{data}$, and outputs an (nth−1) magnitude error data sample $ec_{data}$ on the output 54. The adaptive filter 36 of the cardiac artifact cancellation component 26 receives the nth acquired data sample $y_{data}$ from the signal acquisition module 20 at the first input 56a, receives the (nth−1) magnitude error data sample $ec_{data}$ from the signal comparator 38 at the second input 56b, varies its transfer function in response to the (nth−1) magnitude error data sample $ec_{data}$, and filters the nth acquired data sample $y_{data}$ in accordance with the varied transfer function, thereby generating an nth estimated cardiac artifact data sample $Cest_{data}$. The second signal comparator 40 of the cardiac artifact cancellation component 26 receives the nth acquired data sample $y_{data}$ from the signal acquisition module 20 at the first input 60a, receives the nth estimated cardiac artifact data sample $Cest_{data}$ from the adaptive filter 36' at the second input 60b, computes the difference between the magnitude of the nth acquired data sample $y_{data}$ and the magnitude of the nth estimated cardiac artifact data sample $Cest_{data}$, and outputs an nth reduced-artifact data sample $y'_{data}$.

Then, the first signal comparator 38 receives the nth reference data sample $r_{data}$ from the PLL component 22 at the first input 52a, receives an (nth+1) estimated cardiac artifact data sample $Cest_{data}$ from the adaptive filter 36 at the second input 52b, computes the difference between the magnitude of the nth reference data sample $r_{data}$ and the magnitude of the (nth+1) estimated cardiac artifact data sample $Cest_{data}$, and outputs an nth magnitude error data sample $ec_{data}$ on the output 54. The adaptive filter 36 receives the (nth+1) acquired data sample $y_{data}$ from the signal acquisition module 20 at the first input 56a, receives the nth magnitude error data sample $ec_{data}$ from the signal comparator 38 at the second input 56b, varies its transfer function in response to the nth magnitude error data sample $ec_{data}$, and filters the (nth+1) acquired data sample $y_{data}$ in accordance with the varied transfer function, thereby generating an (nth+1) estimated cardiac artifact data sample $Cest_{data}$. The second signal comparator 40 receives the (nth+1) acquired data sample $y_{data}$ from the signal acquisition module 20 at the first input 60a, receives the (nth+1) estimated cardiac artifact data sample $Cest_{data}$ from the adaptive filter 36 at the second input 60b, computes the difference between the magnitude of the (nth+1) acquired data sample $y_{data}$ and the magnitude of the (nth+1) estimated cardiac artifact data sample $Cest_{data}$, and outputs an (nth+1) reduced-artifact data sample $y'_{data}$. This process is repeated for subsequently acquired data samples $y_{data}$.

The cardiac artifact cancellation component 26' illustrated in FIG. 9) computes a difference between a magnitude of the acquired signal and a magnitude of an estimated periodic artifact component, thereby generating a magnitude error signal representative of the reduced-artifact signal, varies the transfer function in response to the magnitude error signal (e.g., utilizing an RLS algorithm), and filters the periodic reference signal in accordance with the varied transfer function, thereby generating the estimated periodic artifact component.

In particular, the signal comparator 38' of the cardiac artifact cancellation component 26' receives the nth acquired data sample $y_{data}$ from the signal acquisition module 20 at the first input 68a, receives the nth estimated cardiac artifact data sample $Cest_{data}$ from the adaptive filter 36' at the second input 68b, computes the difference between the magnitude of the nth acquired data sample $y_{data}$ and the magnitude of the nth estimated cardiac artifact data sample $Cest_{data}$, and outputs an nth magnitude error data sample $ec_{data}$ as the nth reduced-artifact data sample $y'_{data}$ at the output 70. The adaptive filter 36' of the cardiac artifact cancellation component 26' receives the (nth−1) reference data sample $r_{data}$ from the PLL component 22 at the first input 72a, receives the nth magnitude error data sample $ec_{data}$ from the signal comparator 42, varies its transfer function in response to the nth magnitude error data sample $ec_{data}$, and filters the (nth−1) reference data sample $r_{data}$ in accordance with the varied transfer function, thereby generating the nth estimated cardiac artifact data sample $Cest_{data}$.

Then, the signal comparator 38' receives the (nth+1) acquired data sample $y_{data}$ from the signal acquisition module 20 at the first input 68a, receives the (nth+1) estimated cardiac artifact data sample $Cest_{data}$ from the adaptive filter 36' at the second input 68b, computes the difference between the magnitude of the (nth+1) acquired data sample $y_{data}$ and the magnitude of the (nth+1) estimated cardiac artifact data sample $Cest_{data}$, and outputs an (nth+1) magnitude error data sample $ec_{data}$ as the (nth+1) reduced-artifact data sample $y'_{data}$ at the output 70. The adaptive filter 36' receives the nth reference data sample $r_{data}$ from the PLL component 22 at the first input 72a, receives the (nth+1) magnitude error data sample $ec_{data}$ from the signal comparator 38', varies its transfer function in response to the (nth+1) magnitude error data sample $ec_{data}$, and filters the nth reference data sample $r_{data}$ in accordance with the varied transfer function, thereby generating the (nth+1) estimated cardiac artifact data sample $Cest_{data}$. This process is repeated for subsequently acquired data samples $y_{data}$.

Next, the signal processor 30 determines an existence and location of physiological activity in the user 12, and in particular, neural activity in the cortical region of the brain 14 of the user 12, based on the reduced-artifact signal (step 214). In the illustrated embodiment, the signal processor 30 receives a series of reduced-artifact data sample y'$_{data}$ from the cardiac artifact cancellation component 26 (or 26') at the first input 64a, and determines the existence and location of neural activity in the cortical region of the brain 14 of the user 12, based on the reduced-artifact data sample y'$_{data}$ (step 216). The signal processor 30 optionally determines an existence of neural activity in the sub-cortical region of the brain 14 of the user 12 based on the HR information (step 216). In the illustrated embodiment, the signal processor 30 receives the HR information from the HR computation component 24 at the second input 64b, and determines the existence of neural activity in the sub-cortical region of the brain 14 of the user 12.

The signal processor 30 then generates commands CMD based on the determined neural activity in the cortical region of the brain 14 of the user 12, and optionally the sub-cortical region of the brain 14 of the user 12, and outputs the commands CMD at the output 66 to the external device 16 (step 218).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A physiological activity detection system, comprising:
   a signal acquisition module configured for non-invasively acquiring a signal from an anatomical structure of a user, the acquired signal having a physiological-encoded component and a periodic artifact component that dominates the physiological-encoded component;
   a phase-locked loop (PLL) component configured for estimating a phase of the periodic artifact component of the acquired signal, and generating a periodic reference signal having a phase representative of the estimated phase of the periodic artifact component of the acquired signal; and
   an artifact cancellation component configured for generating an estimated periodic artifact component by scaling and offsetting the periodic reference signal to the periodic artifact component in the acquired signal, and filtering the periodic artifact component from the acquired signal based on the estimated periodic component, thereby yielding a reduced-artifact signal.

2. The physiological activity detection system of claim 1, wherein the anatomical structure of the user is a brain, and wherein the physiological-encoded component is a neurological-encoded component.

3. The physiological activity detection system of claim 2, wherein the periodic artifact component is a cardiac artifact component.

4. The physiological activity detection system of claim 2, wherein the acquired signal comprises signal light.

5. The physiological activity detection system of claim 4, wherein the signal acquisition module is configured for non-invasively acquiring the signal light from the brain of the user via functional near-infrared spectroscopy (fNIRS).

6. The physiological activity detection system of claim 1, wherein the periodic reference signal varies in accordance with a sine wave.

7. The physiological activity detection system of claim 1, wherein the signal acquisition module is configured for digitizing the acquired signal into acquired data, and wherein the PLL component is configured for estimating the phase of the periodic artifact component in the acquired data, and generating periodic reference data having a phase representative of the estimated phase of the periodic artifact component in the acquired data.

8. The physiological activity detection system of claim 7, wherein the acquired data comprises a time-series of data samples, and the PLL component is configured for respectively estimating phases of the periodic artifact component in the acquired data samples, and generating periodic reference data samples respectively having phases representative of the estimated phases of the periodic artifact component in the acquired data samples.

9. The physiological activity detection system of claim 1, wherein the PLL component comprises:
   a phase comparator; and
   a voltage-controlled oscillator (VCO) arranged in a closed feedback loop with the phase comparator;
   wherein the phase comparator is configured for computing a difference between the phase of the periodic artifact component of the acquired signal and the phase of the periodic reference signal, thereby respectively generating a phase error signal; and
   wherein the VCO is configured for generating the periodic reference signal, and varying the frequency of the periodic reference signal in accordance with the phase error signal, thereby varying the phase of the periodic reference signal.

10. The physiological activity detection system of claim 1, further comprising a frequency computation component configured for computing a frequency of the periodic artifact component.

11. The physiological activity detection system of claim 10, wherein the periodic artifact component is a cardiac artifact component, the frequency computation component is a heart rate (HR) computation component, and the computed frequency of the cardiac artifact component is a heart rate (HR) of the user.

12. The physiological activity detection system of claim 1, wherein the artifact cancellation component is configured for filtering the periodic artifact component from the acquired signal by subtracting the estimated periodic artifact component from the acquired signal, thereby yielding the reduced-artifact signal.

13. The physiological activity detection system of claim 1, wherein the physiological-encoded component dominates the periodic artifact component in the reduced-artifact signal.

14. The physiological activity detection system of claim 1, wherein the periodic artifact component is substantially eliminated from the reduced-artifact signal.

15. The physiological activity detection system of claim 1, further comprising a signal processor configured for determining an existence of physiological activity in the user based on the reduced-artifact signal.

16. The physiological activity detection system of claim 15, wherein the anatomical structure of the user is a brain, the physiological-encoded component is neurological-encoded component, and the physiological activity is neural activity.

17. The physiological activity detection system of claim 16, wherein the neural activity is within cortical region of the brain of the user, wherein the periodic artifact component is a cardiac artifact component, and the physiological activity detection system further comprises a heart rate (HR) computation component configured for computing a heart rate (HR) of the user based on the phase of the periodic reference signal, wherein the signal processor is configured for determining an existence of neural activity in subcortical region of the brain of the user based on the computed HR of the user.

18. The physiological activity detection system of claim 1, wherein the artifact cancellation component comprises:
a first signal comparator;
an adaptive filter arranged in a feedback loop with the first signal comparator; and
a second signal comparator;
wherein the first signal comparator is configured for computing a difference between a magnitude of the estimated periodic artifact component and a magnitude of the periodic reference signal, thereby generating a magnitude error signal;
wherein the adaptive filter is configured for varying a transfer function in response to the magnitude error signal, and filtering the acquired signal in accordance with the varied transfer function, thereby generating the estimated periodic artifact component;
wherein the second signal comparator is configured for computing the difference between a magnitude of the acquired signal and a magnitude of the estimated periodic artifact component to yield the reduced-artifact signal.

19. The physiological activity detection system of claim 1, wherein the artifact cancellation component comprises:
a signal comparator;
an adaptive filter arranged in a feedback loop with the first signal comparator;
wherein the signal comparator is configured for computing a difference between a magnitude of the acquired signal and a magnitude of the estimated periodic artifact component, thereby generating a magnitude error signal representative of the reduced-artifact signal;
wherein the adaptive filter is configured for varying a transfer function in response to the magnitude error signal, and filtering the periodic reference signal in accordance with the varied transfer function, thereby generating the estimated periodic artifact component.

20. The physiological activity detection system of claim 1, wherein the artifact cancellation component is configured for utilizing a recursive least squares (RLS) algorithm to map the periodic reference signal to the acquired signal by varying a transfer function.

21. A method of detecting physiological activity in an anatomical structure of a person, comprising:
non-invasively acquiring a signal from the anatomical structure of the person, the acquired signal having a physiological-encoded component and a periodic artifact component that dominates the physiological-encoded component; and
computing a difference between an actual phase of the periodic artifact component of the acquired signal and an estimated phase of the periodic artifact component of the acquired signal, thereby generating a phase error signal; and
updating the estimated phase of the periodic artifact component of the acquired signal based on the phase error signal;
repeating the phase difference computation and estimated phase updating steps;
generating a periodic reference signal having a phase equal to the estimated phase of the periodic artifact component of the acquired signal;
generating an estimated periodic artifact component by scaling and offsetting the periodic reference signal to the periodic artifact component in the acquired signal; and
removing at least a portion of the periodic artifact component from the acquired signal based on the estimated periodic artifact component, thereby yielding a reduced-artifact signal.

22. The method of claim 21, wherein the anatomical structure of the user is a brain of the user, and wherein the physiological-encoded component is a neurological-encoded component.

23. The method of claim 22, wherein the periodic artifact component is a cardiac artifact component.

24. The method of claim 22, wherein the acquired signal comprises signal light.

25. The method of claim 24, wherein signal light is non-invasively acquired from the brain of the user via functional near-infrared spectroscopy (fNIRS).

26. The method of claim 21, wherein the periodic reference signal varies in accordance with a sine wave.

27. The method of claim 21, further comprising digitizing the acquired signal into acquired data, wherein the periodic reference signal comprises periodic reference data.

28. The method of claim 27, wherein the acquired data comprises a time-series of acquired data samples, and the periodic reference data comprises a time-series of periodic reference data samples.

29. The method of claim 21, wherein the phase error generation step and estimated phase updating step comprises:
computing a difference between the phase of the periodic artifact component of the acquired signal and the phase of the periodic reference signal, thereby respectively generating the phase error signal; and
varying the frequency of the periodic reference signal in accordance with the phase error signal, thereby varying the phase of the periodic reference signal.

30. The method of claim 21, further comprising deriving a frequency of the periodic artifact component from the phase of the periodic reference signal.

31. The method of claim 30, wherein the periodic artifact component is a cardiac artifact component, and the derived frequency of the periodic artifact component is a heart rate (HR) of the user.

32. The method of claim 21, wherein removing the at least a portion of the periodic artifact component from the acquired signal comprises subtracting the estimate cardiac component from the acquired signal, thereby yielding the reduced-artifact signal.

33. The method of claim 21, wherein the physiological-encoded component dominates the periodic artifact component in the reduced-artifact signal.

34. The method of claim 21, wherein the periodic artifact component is substantially eliminated from the reduced-artifact signal.

35. The method of claim 21, further comprising determining an existence of physiological activity in the user based on the reduced-artifact signal.

36. The method of claim 35, wherein the anatomical structure of the user is a brain of the user, the physiological-encoded component is neurological-encoded component, and the physiological activity is neural activity.

37. The method of claim 36, wherein the neural activity is within cortical region of the brain of the user, wherein the periodic artifact component is a cardiac artifact component, and the method further comprises computing a heart rate (HR) of the user based on the phase of the periodic reference signal, and determining an existence of neural activity in subcortical region of the brain of the user based on the computed HR of the user.

38. The method of claim 21, wherein removing at least a portion of the periodic artifact component from the acquired signal comprises:
   computing a difference between a magnitude of an estimated periodic artifact component and a magnitude of the periodic reference signal, thereby generating a magnitude error signal;
   varying a transfer function in response to the magnitude error signal;
   filtering the acquired signal in accordance with the varied transfer function, thereby generating the estimated periodic artifact component; and
   computing the difference between a magnitude of the acquired signal and a magnitude of the estimated periodic artifact component to yield the reduced-artifact signal.

39. The method of claim 21, wherein removing at least a portion of the periodic artifact component from the acquired signal comprises:
   computing a difference between a magnitude of the acquired signal and a magnitude of an estimated periodic artifact component, thereby generating a magnitude error signal representative of the reduced-artifact signal;
   varying a transfer function in response to the magnitude error signal; and
   filtering the periodic reference signal in accordance with the varied transfer function, thereby generating the estimated periodic artifact component.

40. The method of claim 21, wherein removing the at least portion of the periodic artifact component from the acquired signal comprises utilizing a recursive least squares (RLS) algorithm to map the periodic reference signal to the acquired signal by varying a transfer function.

* * * * *